(12) United States Patent
Biard et al.

(10) Patent No.: US 7,973,155 B2
(45) Date of Patent: Jul. 5, 2011

(54) STABLE AND LONG-LASTING SIRNA EXPRESSION VECTORS AND THE APPLICATIONS THEREOF

(75) Inventors: Denis Biard, Thiais (FR); Jaime F. Angulo-Mora, Limours (FR)

(73) Assignee: Commissariat a l'Energie Atomique, Paris (FR)

( * ) Notice: Subject to any disclaimer, the term of this patent is extended or adjusted under 35 U.S.C. 154(b) by 621 days.

(21) Appl. No.: 11/884,280

(22) PCT Filed: Feb. 14, 2006

(86) PCT No.: PCT/FR2006/000330
§ 371 (c)(1),
(2), (4) Date: Nov. 27, 2007

(87) PCT Pub. No.: WO2006/085016
PCT Pub. Date: Aug. 17, 2006

(65) Prior Publication Data
US 2010/0048670 A1    Feb. 25, 2010

(30) Foreign Application Priority Data

Feb. 14, 2005  (FR) ..................................... 05 01483

(51) Int. Cl.
*C07H 21/04*     (2006.01)
*C12N 15/63*     (2006.01)
*C12N 15/85*     (2006.01)

(52) U.S. Cl. ..................... 536/24.5; 435/320.1; 435/325
(58) Field of Classification Search .................. None
See application file for complete search history.

(56) References Cited

FOREIGN PATENT DOCUMENTS

EP          1 484 393       12/2004

OTHER PUBLICATIONS

Biard, Denis S. F. et al.," Development of New EBV-Based for Stable Expression of Small Interfering RNa to Mimick Human Syndromes: Application to NNER Gene Silencing", Mol. Cancer Rec., vol. 3, No. 9. pp. 519-529, 2005. XP002349462.

Miyagishi, M. et al.," Expressions of siRNA from a pol III Promoter in Mammalian Cells", Perspectives in Gene Expression, pp. 361-375, 2003. XP001246949.

Brummelkamp, T. R. et al.,"A System for Stable Expression of Short Interfering RNAs in Mammalian Cells", Science, vol. 296, No. 5567, pp. 550-553, 2002. XP002225638.

Database Google "Invitrogen Life Technologies" HTTP://WWW.INVITROGEN.COM/CONTENT/SFS/VECTORS/PCDNA3.PDF, PDF Data Sheet, 2006. XP002386946.

Biard, D. S. F. et al.,"Regulation of the *Escherichia Coli* Lac Operon Expressed in Human Cells", Biochimica et Biophisica Acta, vol. 1130, No. 1, pp. 68-74, 1992. XP009055483.

Biard, D. S. F. et al.,"Establishment of a Human Cell Line for the Detection of Demethylating Agents", Experimental Cell Research, vol. 200, No. 2, pp. 263-271, 1992. XP 009055400.

Chittenden, T. et al.,"Functional Limits of oriP, the Epstein-Barr Virus Plasmid Origin of Replication", Journal of Virology, vol. 63, No. 7, pp. 3016-3025, 1989. XP 002914212.

*Primary Examiner* — Amy Bowman
(74) *Attorney, Agent, or Firm* — Oblon, Spivak, McClelland, Maier & Neustadt, L.L.P.

(57) ABSTRACT

The invention relates to a siRNA expression vector that can inhibit or eliminate the expression of a target gene in a mammalian cell, said vector comprising: a bacterial cassette containing a bacterial origin of replication and a bacterial selection marker M1; a eucaryotic cell selection cassette comprising a marker M2 for selecting eucaryotic cells under the control of an appropriate promoter; a cassette EBV comprising at least one fragment of the antigen EBNA-1, at least one fragment FR, and at least one fragment of the region DYAD; and a siRNA transcription cassette comprising at least one region coding for a siRNA corresponding to the target gene to be inhibited or eliminated, under the control of elements for regulating transcription in mammalian cells, said regulating elements including at least one promoter capable of transcribing a siRNA in mammalian cells, and a transcription terminator. The invention also relates to the applications of one such expression vector.

11 Claims, 25 Drawing Sheets

Figure 1B:
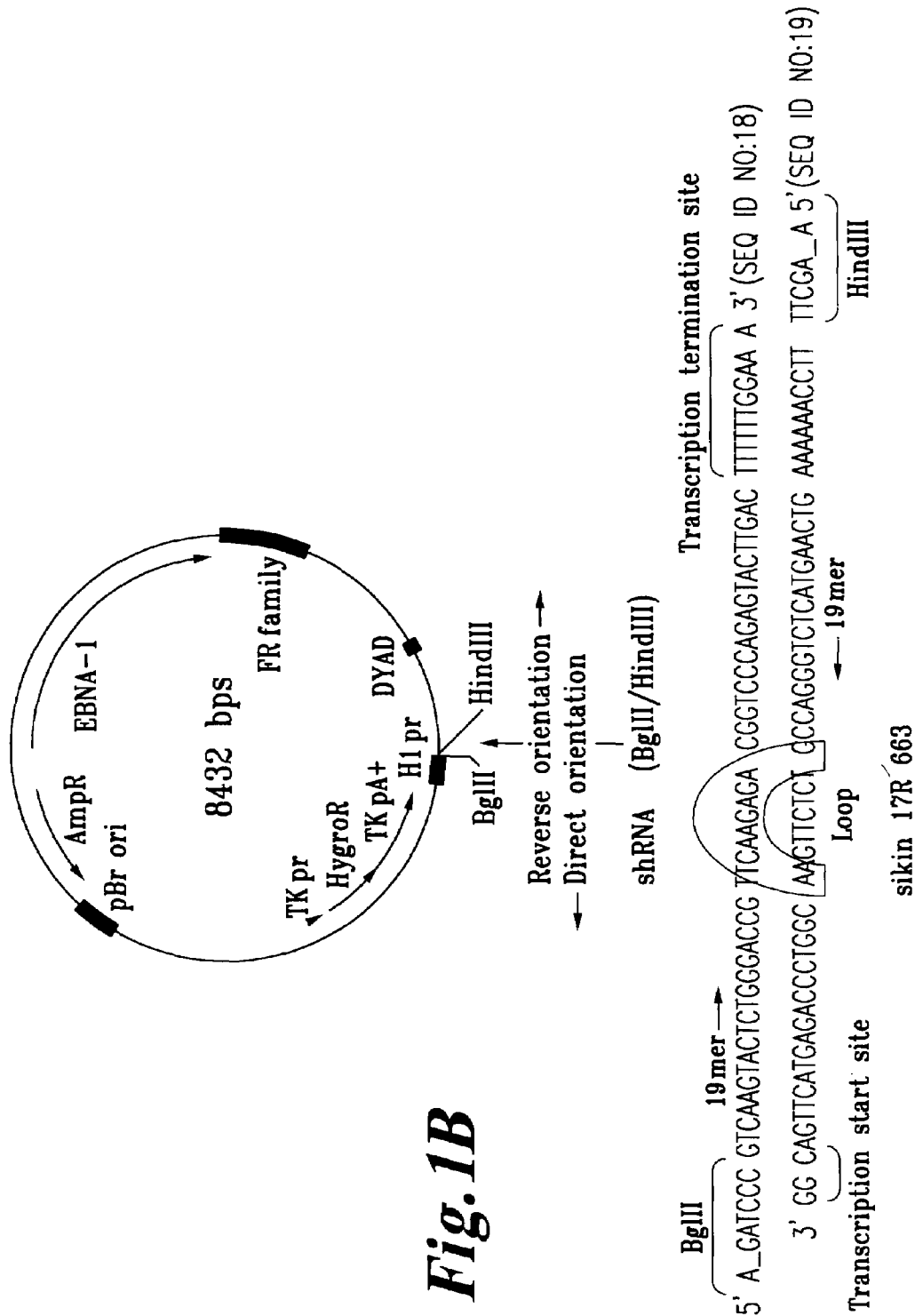

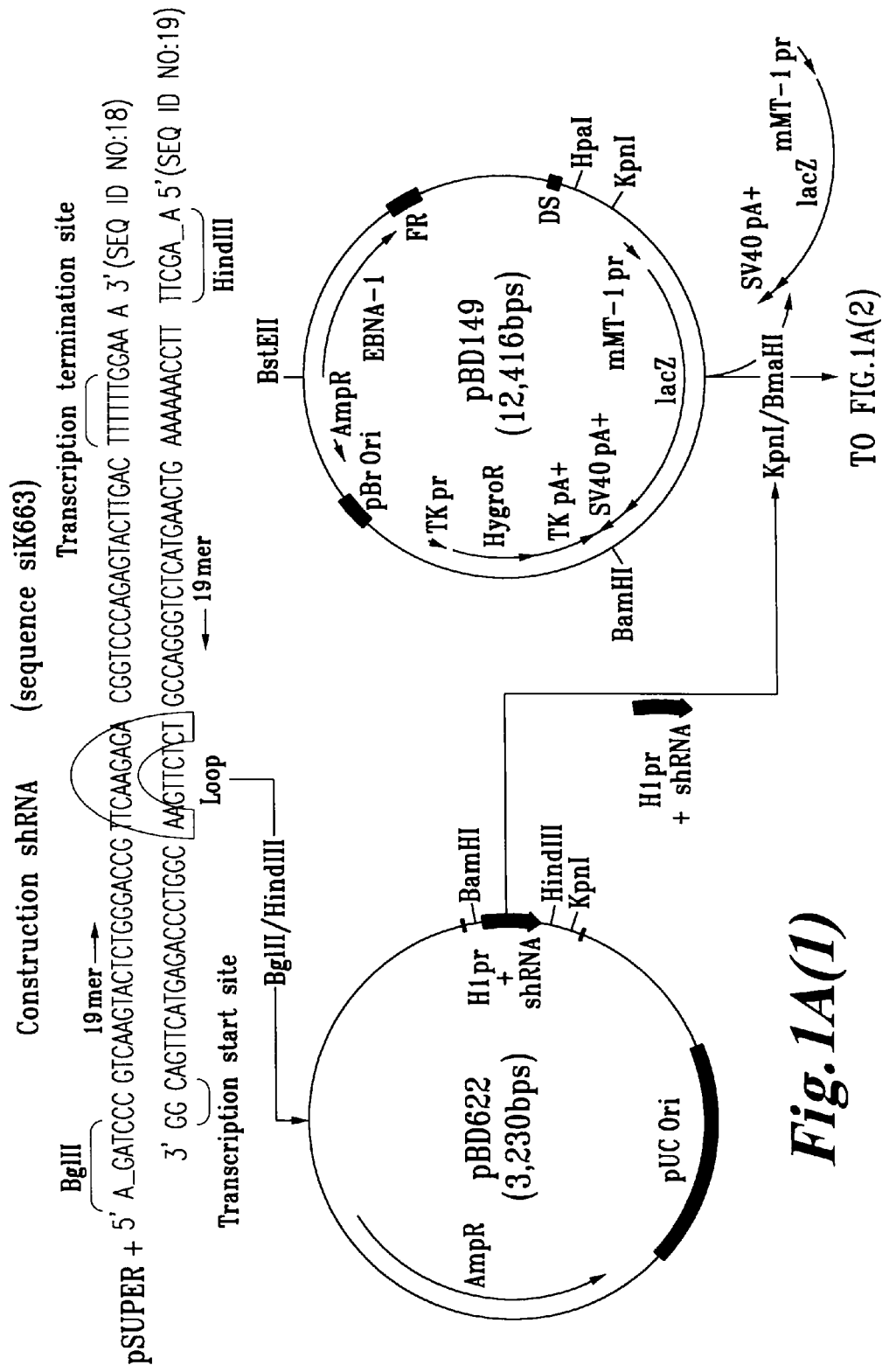
Fig. 1A(1)

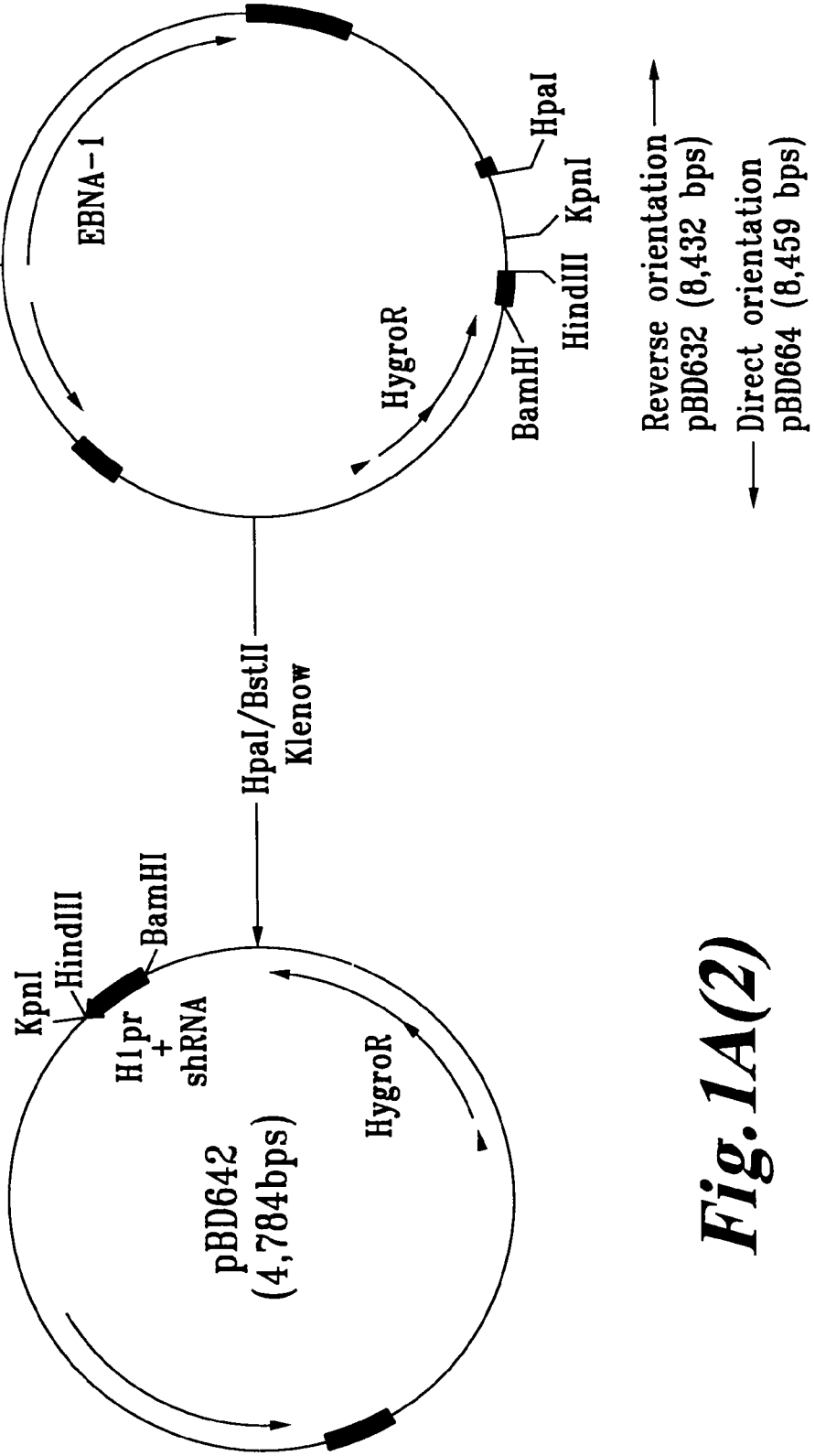
Fig. 1A(2)

117 days after transfection

Southern blotting analysis

STABLE AND LONG-LASTING SIRNA EXPRESSION VECTORS AND THE APPLICATIONS THEREOF

The present invention relates to the field of RNA interference, and more particularly to the development of stable and long-lasting interfering RNA (siRNA) expression vectors and to uses thereof.

The invention therefore also relates to human or nonhuman cells and nonhuman transgenic animals which comprise said vector and also to the uses thereof for evaluating the activity of siRNAs and validating them as a medicament and in human therapy.

It has been shown that small fragments of double-stranded RNA of 21 to 25 nucleotides, complementary to an mRNA, are, when they are introduced into eukaryotic cells, capable of greatly inhibiting the expression of the corresponding gene by destroying this mRNA (for a review, see Biofutur (33), Voorhoeve et al. (34)). This phenomenon of specific inhibition or extinction of gene expression, called RNA interference (RNAi), opens up advantageous perspectives in many fields; in particular, in the field of functional genomics and of pharmaceutical research, small interfering RNAs (or silencing inducing RNAs), referred to as siRNAs, are useful respectively for identifying the function of new genes and for selecting target genes and candidate medicaments. In addition, siRNAs can also be used directly as medicaments.

Thus, siRNAs specific for transcripts encoding viral or cell proteins and capable of inhibiting the production of the corresponding proteins have been described.

More specifically, the process of RNA interference essentially comprises several steps and appears to be initiated by the processive cleavage of long segments of double-stranded RNA into double-stranded fragments of 21 to 25 nucleotides (siRNAs). These siRNA duplexes, produced by the DICER enzyme (RNaseIII of the family of specific dsRNA endonucleases), are incorporated into a RISC or RNA Induced Silencing Complex which recognizes and cleaves a target RNA complementary to one strand of the siRNA and which therefore brings about the degradation of a specific mRNA.

siRNAs act at low concentrations, and can be expressed intracellularly, in particular from RNA polymerase III (Pol III) promoters.

At the current time, three different approaches exist for extinguishing or inhibiting the expression of a gene in mammalian cells, and in particular human cells, using the RNA interference technique: (1) transfection of siRNA duplex, (2) transfection of nonviral expression vectors and (3) infection with recombinant viruses.

(1) siRNA Duplex

Many documents describe the direct administration of a double-stranded RNA duplex (siRNA), in particular by transfection {(Soutschek J. et al. (27); Elbashir S M. et al. (3); Bantounas I. et al. (28)}. Although this approach is extremely effective, it has the following drawbacks: (i) the siRNA duplexes are unstable and generally expensive; (ii) the transfection is transient and does not therefore allow medium- and long-term studies; (iii) the cost makes this approach impossible if the intention is to work on a very large number of cells (in the context of a multiprotein complex purification study, for example).

(2) and (3) Integrative Nonviral Expression Vectors and Viral Vectors

The short lifespan of siRNAs in vivo has lead various teams of researchers working on this subject to develop systems based on vectors which must enable a more stable expression of the siRNAs in mammalian cells.

With this aim, certain authors have developed integrative expression vectors (plasmids) (Barquinero J. et al. (30)) or viral vectors (essentially retroviruses, lentiviruses or adenoviruses). These vectors have the advantage of being adaptable. Thus, the cells will be either transfected (plasmids) or infected (viral vectors).

These (plasmid or viral) vectors use the same strategy for expression of the siRNA sequence: within the vector, a DNA sequence will encode an RNA which will have a hairpin structure (shRNA for small hairpin RNA). Tandem structures (a priori less effective) have also been envisioned. In the case of the expression of an shRNA structure, the strategy implemented involves, for example, the cloning of a sense sequence corresponding to the future siRNA, followed by a spacer arm or loop and by the antisense sequence of said siRNA, followed by a series of T residues (polyU in the final siRNA). During the in situ synthesis of this shRNA sequence, the presence of the spacer arm will lead to the formation of a hairpin structure (shRNA) which will allow the sense and antisense sequences of the future siRNA to pair. This hairpin structure will be recognized by an endogenous RNase III (DICER), which will cleave it so as to generate a functional siRNA.

In order to allow effective transcription of these very small RNA structures, it has been recommended to use promoters specific for RNA polymerase III (Pol III promoters), such as the U6, H1 or tRNA promoters. It should be noted that the RNA Pol III is specialized in the transcription of small noncoding RNAs such as tRNAs, which have transcription termination sites perfectly defined by sequences of 4 to 6 thymidines (Sui G. et al. (35)). However, this does not exclude the use of RNA Pol II specific promoters, such as the human CMV IE enhancer/promoter (cytomegalovirus immediate-early gene enhancer/promoter) or modified CMV promoters such as those described in the literature (Dubois-Dauphin, 2004 (36); Hu et al. 2004 (37); Liu et al. 2004 (38), Sato et al. 2003 (39)).

Expression vector: Thus, Brummelkamp et al. (5) have described an integrative plasmid (pSUPER), which contains a Pol III HI promoter capable of directing the transcription of hairpin RNA (shRNA) so as to bring about the in situ synthesis of a functional siRNA. However, this integrative plasmid has the following drawbacks:

It does not make it possible to obtain transient inhibition or extinction.

It is present in the transfected cells at very high copy numbers per cell; this can saturate the RNAi machinery (for example, the RISC complex) and cause adverse effects (6).

It integrates anywhere in the genome and can therefore induce, in addition to the adverse effects, parasitic effects.

This plasmid has subsequently been modified so as to insert therein a prokaryotic selectable marker (geneticin, for example). However, most authors use these vectors only in transient transfection trials, and only a few rare clones have been described after several days of culture (7-9).

Viral vectors: these vectors allow the infection of target cells that are difficult to transfect (Dykxhoorn D. et al. (29); Barquinero J. et al. (30)). Such viral vectors allow effective targeting and an a priori medium-term expression in the target cells. Their advantage in in vivo approaches in mice has also been emphasized. However, the great disadvantage of these recombinant viruses is that they pose real safety problems since most laboratories are not equipped to work, under the rules of the art, with these viruses. Their use for evaluating siRNAs is therefore not always advantageous.

Thus, if one excludes viral vectors, for reasons of safety, RNA interference trials in human cells in culture are based mainly on transient transfections of double-stranded RNA or of integrative plasmids. In this context, it is difficult to isolate stable clones. Consequently, it has been possible to effectively maintain in culture very few clones, and only for very limited periods of time (a few days) (7-9), although there exists a real need for a stable expression in order to obtain an extensive disruption of the target for the purpose of a long-term evaluation of siRNAs.

Consequently, the present application gave itself the aim of providing vectors which significantly increase the effectiveness of RNAi, said vectors making it possible to obtain effective, specific and very long-term inhibition or extinction of a target gene in human cells.

In fact, it is important to have an effective system of validating the downstream effects mediated by siRNAs, insofar as the results obtained using siRNAs are not always those expected (19), it being possible in particular for siRNAs to induce nonspecific effects at the protein level.

In order to avoid such a situation, the inventors have developed a new construct which is better suited to the practical needs than the constructs of the prior art, in particular:
 in that it allows a very long-term (several months) stable expression of siRNAs in mammalian cells in culture;
 in that it makes it possible to prevent adverse effects related to the saturation of the cellular machinery;
 in that it makes it possible to have a tool for the long-term (several months) study of the phenotypic consequences of the (partial or total) loss of the expression of a gene; this makes it possible to test siRNA probes and to analyze the biological consequences of these probes on cells maintained in culture for a very long time (several months). This makes it possible to implement a method of validating siRNA probes before they are introduced into viral vectors constructed for therapeutic purposes (retroviruses, lentiviruses or adenoviruses);
 in that it makes it possible to mimic human pathologies on cells maintained for a long time in culture (model particularly more flexible than cells obtained by knockout); and
 in that it makes it possible to obtain, for the first time, human cells with virtually identical genomes, i.e. which differ only by virtue of a small shRNA sequence.

Consequently, a subject of the present invention is an siRNA expression vector capable of inhibiting or extinguishing the expression of a target gene (endogenous or exogenous) in a mammalian cell, which vector is characterized in that it comprises:
 (1) a bacterial cassette comprising a bacterial origin of replication and a bacterial selectable marker M1,
 (2) a cassette for selection in eukaryotic cells, comprising a selectable marker M2 for eukaryotic cells, and in particular for mammalian cells, under the control of an appropriate promoter,
 (3) an EBV cassette comprising at least one fragment of the Epstein-Barr virus nuclear antigen 1 (EBNA-1), at least one fragment of the family of repeats (FR) and at least one fragment of the double symmetry (DYAD) region, and
 (4) an siRNA transcription cassette comprising at least one region encoding an siRNA corresponding to the target gene to be inhibited or to be extinguished, under the control of regulatory elements for transcription in mammalian cells, which regulatory elements include at least one promoter capable of transcribing an siRNA in mammalian cells and a transcription terminator.

According to an advantageous embodiment of said vector, the bacterial cassette (1) comprises a bacterial selectable marker M1 selected from the group consisting of markers for resistance to an antibiotic (ampicillin, kanamycin, rifampicin, tetracycline) and auxotrophic markers (TRP1, URA3).

According to another advantageous embodiment of said vector, the cassette for selection in eukaryotic cells (2) comprises a eukaryotic selectable marker M2 selected from the group consisting of markers for resistance to an antibiotic (hygromycin, geneticin, neomycin or G418, puromycin, and zeocin, blasticidin).

According to an advantageous arrangement of this embodiment, said selectable marker M2 is under the control of a suitable promoter selected from the group consisting of the HSV thymidine kinase promoter and the SV40 promoter.

The elements of the EBV cassette (3) are more specifically the following:
The EBNA-1 Nuclear Antigen The EBNA-1 protein contains 641 amino acids with an unusual primary sequence characterized by the presence of numerous repeats. One of them (amino acids 90 to 328) contains exclusively Gly-Gly-Ala repeats. The entire EBNA-1 sequence is not necessary; thus, the EBV vectors according to the invention derive from the vector p205 of Yates et al. (57), in which 700 of the 717 bp of the Gly-Gly-Ala repeat of the B95-8 virus have been deleted. These vectors replicate more effectively than their homologues carrying the entire EBNA-1 gene.

The Latent Infection Phase Origin of Replication (OriP):

The OriP is a region of 1800 bp which contains 2 cis-sequences separated by 960 bp (Yates et al. (40), Sugden et al. (41)): region 1 or family of repeats ("FR" sequence) and region 2 or double symmetry sequence (Dyad sequence).

The family of Repeats ("FR")

The FR sequence is composed of 20 almost perfect copies of a 30 by motif, each copy containing a binding site for the EBNA-1 viral protein. The consensus binding sequence for EBNA-1 is (Rawlins et al. 1985 (42)):

$_5$·AGATTAGGATAGCT.ATGCTACCCAGATAT$_3$· (SEQ ID NO: 20).

In expression vectors, in the presence exclusively of the EBNA-1 protein, the FR region behaves as a powerful transcription enhancer that can increase the activity of a weak promoter such as HSV-TK by a factor of 200 (Reisman et al. 1986 (43)). Moreover, the FR region is involved in replication efficiency and in the determination of cell specificity. While it is absolutely necessary for replication, this sequence alone in the presence of EBNA-1 does not allow replication of the EBV plasmids (Lupton et al. 1985 (44); Reisman et al. 1985 (45)).

The functions of transcription enhancer and of maintaining the genome in episomal form are a highly cooperative process between the various regions of the FR, which involves a minimum sequence or 6 to 7 repeats of the 30 bp motif (Wysokenski et al. 1989 (46)). A smaller number of repeat motifs results in the plasmids no longer being maintained in the episomal form and also a considerable process of structural rearrangement which results in the formation of high-molecular-weight recombinant vectors, which are multimeric head-to-tail forms of the plasmid of origin. These plasmids have found a sufficient number of repeat motifs for them to be maintained extrachromosomally (Chittenden et al. 1989 (47)).

The FR motif contains primary replication termination elements which act, after the binding of EBNA-1, as a barrier for the replication fork (Krysan et al. 1991 (48)). Furthermore, the FR sequence confers on the plasmids the property of retention in the nucleoplasm, even in the absence of the replication of said plasmids (Krysan et al. 1989 (49)).

The Double Symmetry (Dyad) Region

This region of 140 bp contains 2 binding sites for EBNA-1, located symmetrically within a double symmetry region of 65 bp, which form a stem (31 bp)/loop (3 bp) structure. Two other sites border this region.

The binding of the EBNA-1 protein with the Dyad sequence facilitates the initiation of replication close to this element (Rawlins et al. 1985, mentioned above; Reisman et al., 1985, mentioned above; Gahn et al. (50)). This origin of replication is devoid of nucleosomic structure (Sexton et al. (51)), in particular at its 3' end. The deletion of the 3' end of the Dyad sequence or of the entire said sequence completely abolishes the maintaining of EBV genomes in episomal form (Chittenden et al., 1989, mentioned above).

The proximity of elements for termination (FR) and initiation of replication (Dyad) in the oriP results in a mainly unidirectional replication of the DNA in the EBV vectors. The fork progressing toward the FR sequence is stopped at this level, whereas that heading in the opposite direction runs along the plasmid and encounters the awaiting fork in the FR (50). Moreover, it has been proposed that the direction of transcription and the movement of the replication fork can be coordinated.

According to another advantageous embodiment of said vector, the promoter capable of transcribing an siRNA in mammalian cells is a promoter of RNA polymerase III (type 1, 2 or 3) or a promoter recognized by RNA polymerase II, such as the human CMV IE enhancer/promoter (cytomegalovirus immediate-early gene enhancer/promoter) or modified CMV promoters such as those described in the literature (Dubois-Dauphin et al. (36); Hu et al. (37); Liu et al. (38); Sato et al. (39)).

It is functionally linked with the region encoding the siRNA. The sequences encoding the siRNA are immediately downstream of the transcription initiation site (CCG, for example) or else a maximum of at most 20 base pairs away from the latter. Other regulator sequences can advantageously be associated with said promoter: sequences which can be induced or modulated (by tetracycline, for example $Tet^{ON/OFF}$, by IPTG or lactose, for example the lacO operator, by temperature or by chemical or physical genotoxics) or tissue-specific sequences by optionally choosing RNA polymerase type II promoters; in this case, preference may be given to shRNA-miR hybrid sequences, in which a structure of shRNA type is introduced into the structure of a microRNA (miRNA) allowing synthesis of the siRNAs by means of RNA polymerase type II-dependent promoters (Sylva et al., Second-generation shRNA libraries covering the mouse and human genomes. Natural. Genet. 2005; 37, 1281-1288).

Said transcription cassette also comprises:
   downstream of the sequence encoding the siRNA, a transcription terminator which preferably comprises a sequence of thymidines, preferably 4-6 thymidines, and even more preferably 6 consecutive thymidines, in the sense strand of the construct, and
   a system of selection for the cloning; to this effect, a prokaryotic promoter (T7, EM7, etc.), followed by the alpha fragment of the LacZ gene (LacZ' or LacZ alpha) is advantageously introduced into the construct and allows the selection in the bacterium. After complementation in host bacteria selected for this purpose, the bacteria carrying the vector of origin will be blue, those carrying a recombinant vector where the LacZ' has been replaced with the shRNA sequence will be white.

This system constitutes a criterion of selection during the insertion of an shRNA sequence.

According to an advantageous arrangement of this embodiment, said RNA polymerase III promoter is selected from the group consisting of the H1 RNA, U6 snRNA, 7SK RNA, 5S, adenovirus VA1, Vault, RNA telomerase and tRNA (Val, Met or Lys3) promoters.

The promoter is preferably the H1 promoter; this promoter controls the expression of H1 RNA, which is the RNA component of human RNAse P.

The sequence selected for the H1 promoter is the following:

(SEQ ID NO: 1)
GGAATTCGAACGCTGACGTCATCAACCCGCTCCAAGGAATCGCGGGCCCA

GTGTCACTAGGCGGGAACACCCAGCGCGCGTGCGCCCTGGCAGGAAGATG

GCTGTGAGGGACAGGGGAGTGGCGCCCTGCAATATTTGCATGTCGCTATG

TGTTCTGGGAAATCACCATAAACGTGAAATGTCTTTGGATTTGGGAATCT

TATAAGTTCTGTATGAGACCAC;

and corresponds to sequence 145-366 of the H1 gene and of its promoter, referenced under accession No. X16612 in the NCBI database.

The present invention thus relates to various constructs capable of producing siRNAs. In these constructs, the cassettes (1) and (2) containing, respectively, the bacterial selectable marker M1 and the eukaryotic selectable marker M2 are preferably in the same orientation.

For the purpose of the present invention, the term "construct" is intended to mean both polynucleotides and vectors.

The constructs according to the invention are replicative constructs which do not saturate the RNAi machinery and which induce an extinction of the target gene in more than 95% of cells, two weeks after the transfection (this depends, however, on the siRNA sequence which was selected), whereas cells transfected with integrative plasmids (carrying a selectable marker) induce less than 50% extinction, under the same conditions.

In addition, and surprisingly, they maintain a target-gene extinction, in various mammalian cell types (HeLa, RKO, MRC5-V2, for example) in culture for periods of greater than 1 year (very good reproducibility).

The region encoding the siRNA corresponds to a double-stranded RNA molecule which comprises a region identical to the target gene. The siRNA is capable of specifically extinguishing or inhibiting the target gene. Many publications provide the information necessary for selecting an siRNA {Gilmore IR et al. (31); Dykxhoorn D. et al., mentioned above (29); Chalk A M et al. (52)}.

The construct according to the invention preferably generates an siRNA from a hairpin precursor RNA (shRNA).

The constructs according to the invention can be introduced into the target cells by various methods of transfection:
   either they are associated with a substance which allows them to cross the target-cell membrane: transporter (nanotransporter), liposome preparation, cationic polymers or calcium (chemical method),
   or they are introduced into the cells by a physical method: electroporation or microinjection,
   or a combination of the two methods is used.

The target genes can be any gene of interest.

The aim of the extinction of the gene can be both therapeutic and in order to study the function of a specific gene or all the implications related with the extinction of said gene. The extinction can thus modify a phenotype.

In the present invention, fourteen target genes have already been tested, five of which have more particularly been studied (XPC, XPA, kin17, DNA PKcs and XRCC4). All these studies show the advantage of the constructs according to the invention.

Two of these genes were selected in such a way that their extinction mimics a human syndrome, in order to evaluate the long-term consequences of the extinction of these genes in syngenic cells.

The XPA (Genbank accession number NM-00380) and XPC (Genbank accession number NM-0004628) proteins are necessary for the recognition and the excision of voluminous DNA lesions during nucleotide excision-resynthesis repair (NER). These proteins are associated with the following pathologies: hereditary sensitivity to sunlight, xeroderma pigmentosum.

The XPC protein is essential for the initial step of recognition of the DNA lesion during global genome repair (GGR) (12). The XPA protein participates in the formation of a preincision complex (13).

Since there exists a genetic interaction between the XPA/XPC proteins and the kin17 protein (Genbank accession number NM-012311) ($_{HSA}$KIN17) (14), vectors for extinction of the KIN17 gene were also prepared. The KIN17 gene encodes a zinc-finger nuclear protein involved in DNA replication and in the cellular response to DNA lesions (15).

The human protein XRCC4 (Genbank accession number NM_022550) is the homologue of the rodent protein "X-ray repair cross-complementing protein 4". The DNA PKcs protein corresponds to the catalytic subunit of the DNA-dependent kinase protein (DNA PK; Genbank accession number NM_006904). XRCC4 acts in concert with DNA ligase IV and with DNA PK in repair processes for double-chain breaks in DNA by NHEJ recombination or V(D)J recombination. It should be noted that the XRCC4 protein is essential to cell survival and that no natural mutant exists.

These two proteins are therefore essential elements of a DNA repair pathway independent of the XPA- and XPC-protein-associated pathway.

A subject of the present invention is also eukaryotic cells, preferably mammalian cells, modified with a vector as defined above.

A subject of the present invention is also a nonhuman transgenic animal, characterized in that it comprises cells modified with a vector as defined above.

A subject of the present invention is also the use of a vector as defined above or of a cell as defined above, for inhibiting or extinguishing the expression of a gene.

A subject of the present invention is also a pharmaceutical composition, characterized in that it comprises a vector as defined above, and at least one pharmaceutically acceptable carrier.

A subject of the present invention is also a method for evaluating the activity of an siRNA capable of inhibiting or extinguishing the expression of a target gene, which method is characterized in that it comprises the following steps:

($a_0$) transfecting at least one mammalian cell with a vector according to the invention, ($b_0$) culturing said cells in a medium capable of selecting the cells resistant to the eukaryotic selectable marker M2, and ($c_0$) analyzing the phenotype of said resistant cells by comparison with the phenotype of nontransfected cells.

A subject of the present invention is also a method for evaluating the activity of a collection of siRNAs designed so as to inhibit or extinguish the expression of a target gene, which method comprises:

($a_1$) preparing a library of vectors according to the invention into which various siRNAs, having the same target gene, are inserted, ($b_1$) transfecting cells with said vectors of said library; each cell or each series of cells being transfected with a different vector, ($c_1$) culturing said cells in a medium capable of selecting the cells resistant to the eukaryotic selectable marker M2, and ($d_1$) analyzing the various phenotypes of said resistant cells.

According to an advantageous embodiment of said methods for evaluating the activity of an siRNA, step ($c_0$) or step ($d_1$) for analyzing the phenotype comprises the detection and/or the quantification of the expression of the target gene.

According to another advantageous embodiment of said methods for evaluating the activity of an siRNA, said methods also comprise, after step ($c_0$) or after step ($d_1$), a step ($c'_0$) or a step ($d'_1$) for culturing said cells in a medium devoid of the element for selecting the cells resistant to the selectable marker M2 and evaluating the restoration of the starting phenotype by reversion.

A subject of the present invention is the use of a cell according to the invention, for evaluating the overall activity of an siRNA.

In fact, the cells according to the invention which can be maintained for a long time in culture make it possible to test siRNA probes and to analyze the biological consequences of these probes in overall terms; this makes it possible in particular to validate siRNA probes before deciding to effectively use them as medicaments.

A subject of the present invention is also a method for screening for molecules capable of treating a disease, comprising the inhibition or the extinction of a gene expressing a protein, which method comprises:

($a_2$) preparing a model for studying said disease by transfecting at least one mammalian cell with a vector according to the invention, comprising an siRNA capable of mimicking said disease, ($b_2$) culturing said cells in a medium capable of selecting the cells resistant to the eukaryotic selectable marker M2, ($c_2$) analyzing the phenotype of said resistant cells by comparison with the phenotype of said cells before transfection, ($d_2$) adding to the culture medium the substance or the library of substances to be screened, ($e_2$) evaluating the modification of the phenotype of said cells, and ($f_2$) selecting the molecules which will restore a normal phenotype and are therefore capable of treating said disease.

The phenotype analyzed will depend on the target gene and on the effects of its extinction.

The ability to evaluate the phenotype of a cell or of an organism according to the invention is advantageous in the context of the various screenings, evaluations and validation of siRNA, such as the ability of a molecule to modulate the phenotype of a cell or of an organism.

In general, for the purpose of the present invention, the term "phenotype" is intended to mean an observable characteristic of an organism or of a cell. In other words, the phenotype is the manifestation of the gene expression in an organism or a cell.

More specifically, a phenotype can correspond to any characteristic of a cell or of an organism which results from the interaction between the genetic profile and the environment.

It may be any manifestation of a disorder or of an infection; it may also be a desired physiological characteristic; it may include biochemical, molecular, cellular or tissue characteristics. The evaluation can be carried out at the genetic level, in particular by investigating whether the expression of a specific gene, other than the gene targeted by the siRNA studied, is modulated, or the evaluation can be carried out by the detection of metabolites specific for the impairment of the gene expression obtained, for instance the expression of a protein, of carbohydrates or of lipids or of other molecules produced by the metabolic pathway inactivated.

The activity of a receptor, of a signal transduction protein, of a membrane channel or of an enzyme can thus be analyzed. At the cellular level, the following functions can be evaluated: migration, adhesion, degranulation, phagocytosis, apoptosis, differentiation, chemotaxis; the transformation of a cell or the acquisition of the tumoral characteristic can also be analyzed.

The various methods according to the invention can advantageously be carried out at high-throughput in multiwell plates.

A subject of the present invention is also a kit, characterized in that it comprises a vector as defined above or cells as defined above, and means for detecting and/or quantifying the expression of a target gene (antibody, in particular, after Western blotting or immunocytochemical labeling).

A subject of the present invention is also an intermediate product for the preparation of a vector as defined above, characterized in that it comprises:

(1) a bacterial cassette comprising a bacterial origin of replication and a bacterial selectable marker M1, (2) a cassette for selection in eukaryotic cells, comprising a selectable marker M2 for eukaryotic cells, and in particular for mammalian cells, under the control of an appropriate promoter, as defined above, (3) an EBV cassette comprising at least one fragment of the Epstein-Barr virus nuclear antigen 1 (EBNA-1), at least one fragment of the family of repeats (FR) and at least one fragment of the double symmetry (DYAD) region, and (4) the H1 promoter and two cloning sites selected in one of the two possible orientations.

According to an advantageous embodiment of said intermediate product, the two cloning sites are Bgl II/Hind III.

According to an advantageous arrangement of this embodiment of said intermediate product, the H1 promoter and the cloning sites are in the direct orientation and the selectable marker M2 is hygromycin, said intermediate product being called pBD665 or pEBV-siD.

According to another advantageous arrangement of this embodiment of said intermediate product, the H1 promoter and the cloning sites are in the inverted (or reverse) orientation and the selectable marker M2 is hygromycin, said intermediate product being called pBD631 or pEBV-siR.

According to another advantageous embodiment of said intermediate product, it comprises a selection system for the cloning, comprising a prokaryotic promoter, in particular the T7 prokaryotic promoter, followed by the alpha fragment of the LacZ gene (LacZ').

According to an advantageous arrangement of this embodiment, the H1 promoter and the cloning sites are in the inverted (or reverse) orientation and the selectable marker M2 is hygromycin, said intermediate product being called pBD751 or pEBVsiR-LacZ' (or pEBVsiR-LacZ'-Hygro).

According to an advantageous arrangement of this embodiment, the H1 promoter and the cloning sites are in the inverted (or reverse) orientation and the selectable marker M2 is puromycin, said intermediate product being called pBD899 or pEBVsiR-LacZ'-Puro.

The latter two intermediate products are cloning vectors and make it possible to target bacteria which carry a recombinant vector; the cloning efficiency is close to 100%. In addition, these two cloning vectors pBD751 and pBD899 are complementary and make it possible to produce double knock-downs.

A subject of the present invention is also a method for preparing a vector according to the invention, characterized in that it comprises:

preparing an intermediate product, as defined above, and inserting a DNA sequence encoding a suitable shRNA into the selected cloning sites.

Figure 1C:
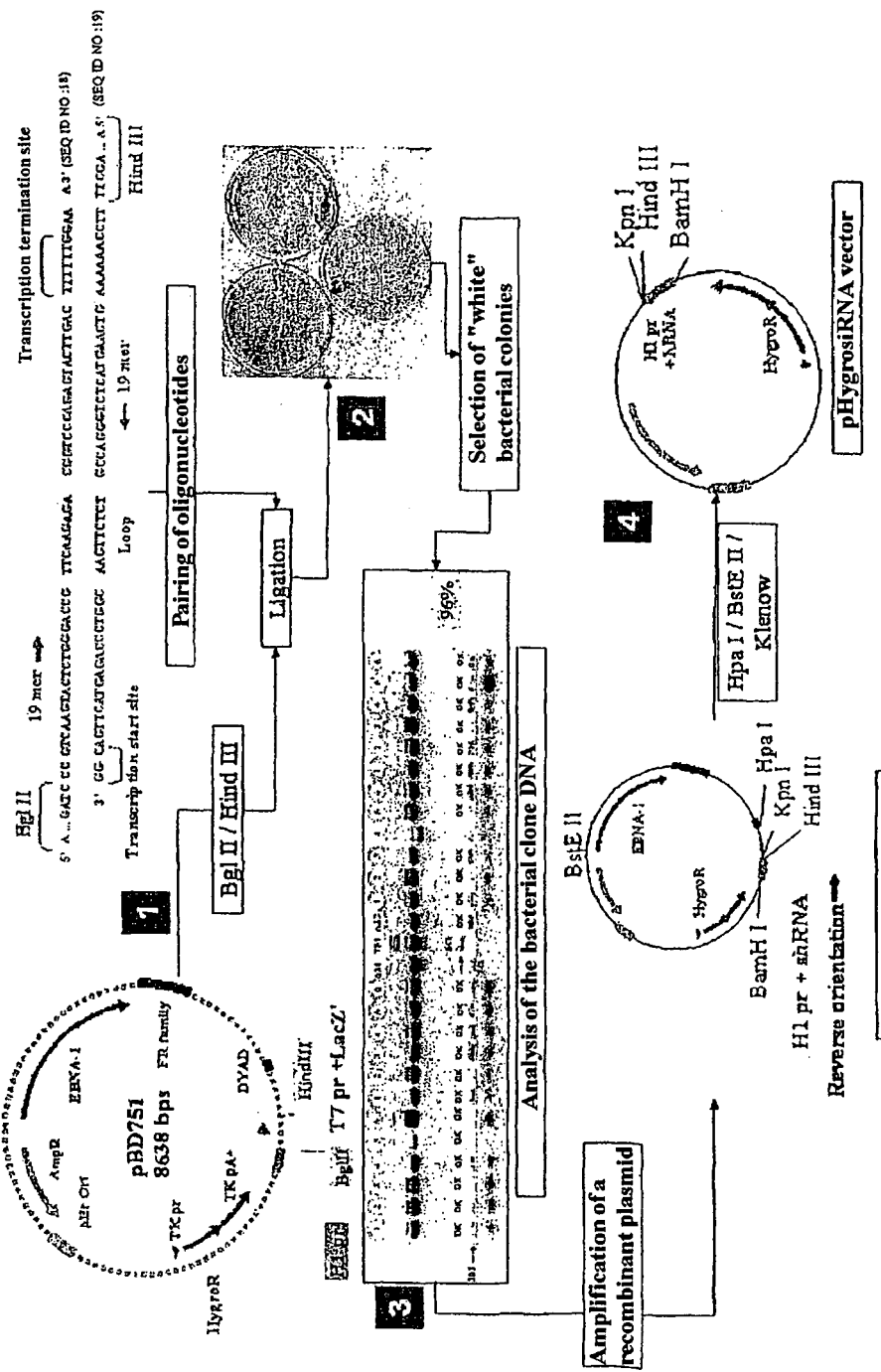

In addition to the above arrangements, the invention also comprises other arrangements which will emerge from the description which follows, which refers to examples of implementation of the method which is the subject of the present invention and also to the table illustrating the sequences of the application and to the attached drawings, in which:

FIG. 1: genetic map of the siRNA vectors. Cloning scheme. Several cloning strategies can be envisaged; indirect cloning (FIG. 1A) and direct cloning (FIG. 1C). A. The BamH I/Kpn I domain of the pSUPER vector (5) containing the Bgl II site, the H1 promoter, an shRNA sequence (or not) and the Hind III site is inserted into an EBV vector (pBD149) (Biard D S et al. (32)), producing the vector pBD631 (cloning vector which does not contain an shRNA sequence and which carries the intact Bgl II and Hind III sites) or the EBV-siRNA vectors specific for a given gene (carrying a specific shRNA sequence and having lost the Bgl II site during cloning).

In comparison, integrative plasmids are obtained after deletion of the EBV segment. A similar strategy is used to obtain an siRNA cassette in the reverse orientation: FR: family of repeat sequences; DS: Dyad symmetry element; HygroR: gene for resistance to hygromycin B; TKpr: HSV virus thymidine kinase promoter; TKPA+: HSV-TK polyadenylation signal; pBrOri: pBR322 origin of replication; AMPr: bacterial β-lactamase gene. B. This figure illustrates the vector pBD632 (=pEBV-siK663R), into which the siRNA (KIN17) sequence is inserted in the reverse orientation:

EBV cassette: EBNA-1+FR+DYAD
siRNA cassette: H1+shRNA
Bacterial cassette: pBrOri+AmpR (=M1)
Eukaryotic resistance cassette: TK promoter+Hygro (M2)+TKpA$^+$.

Figure 2:
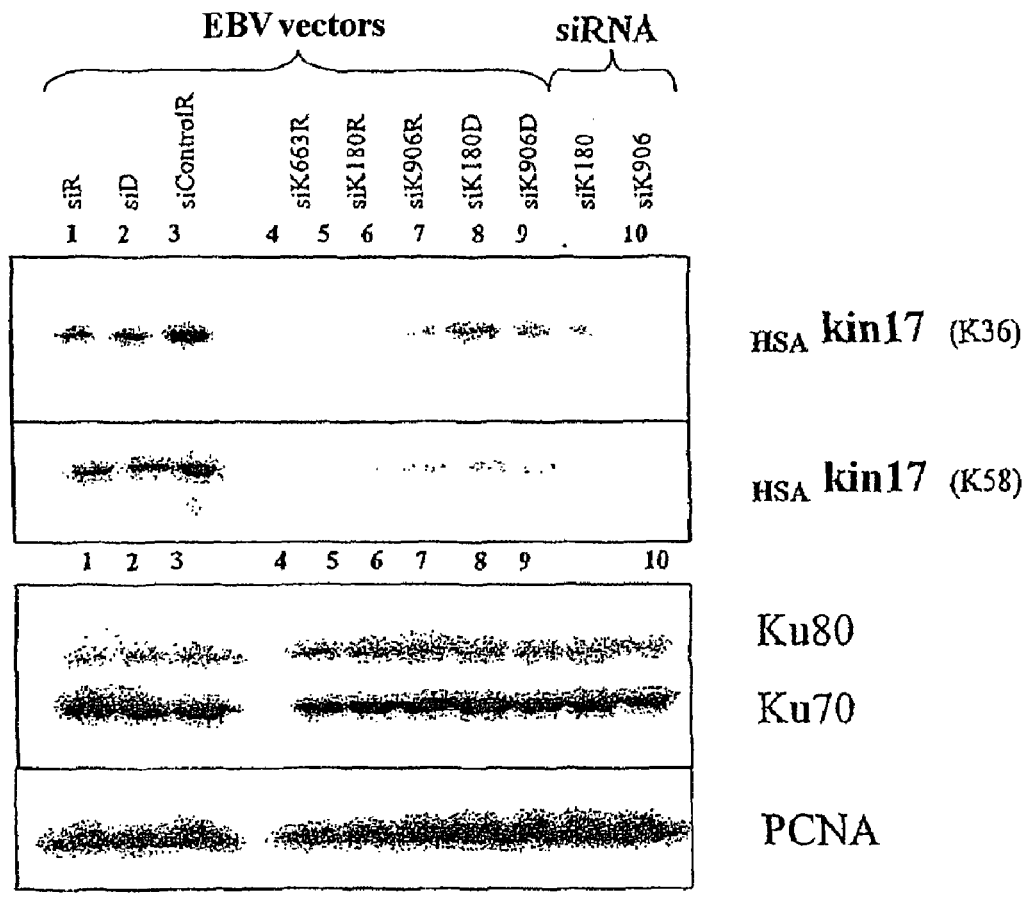
Figure 3:
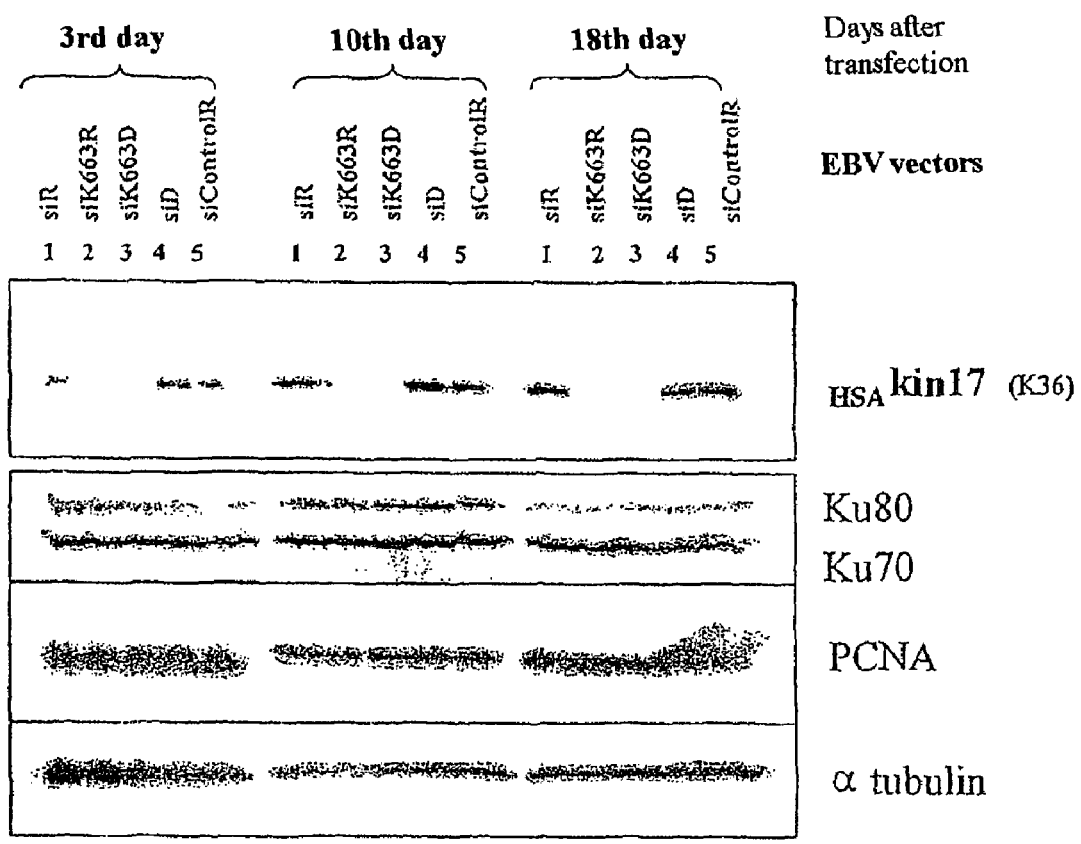
Figure 4:
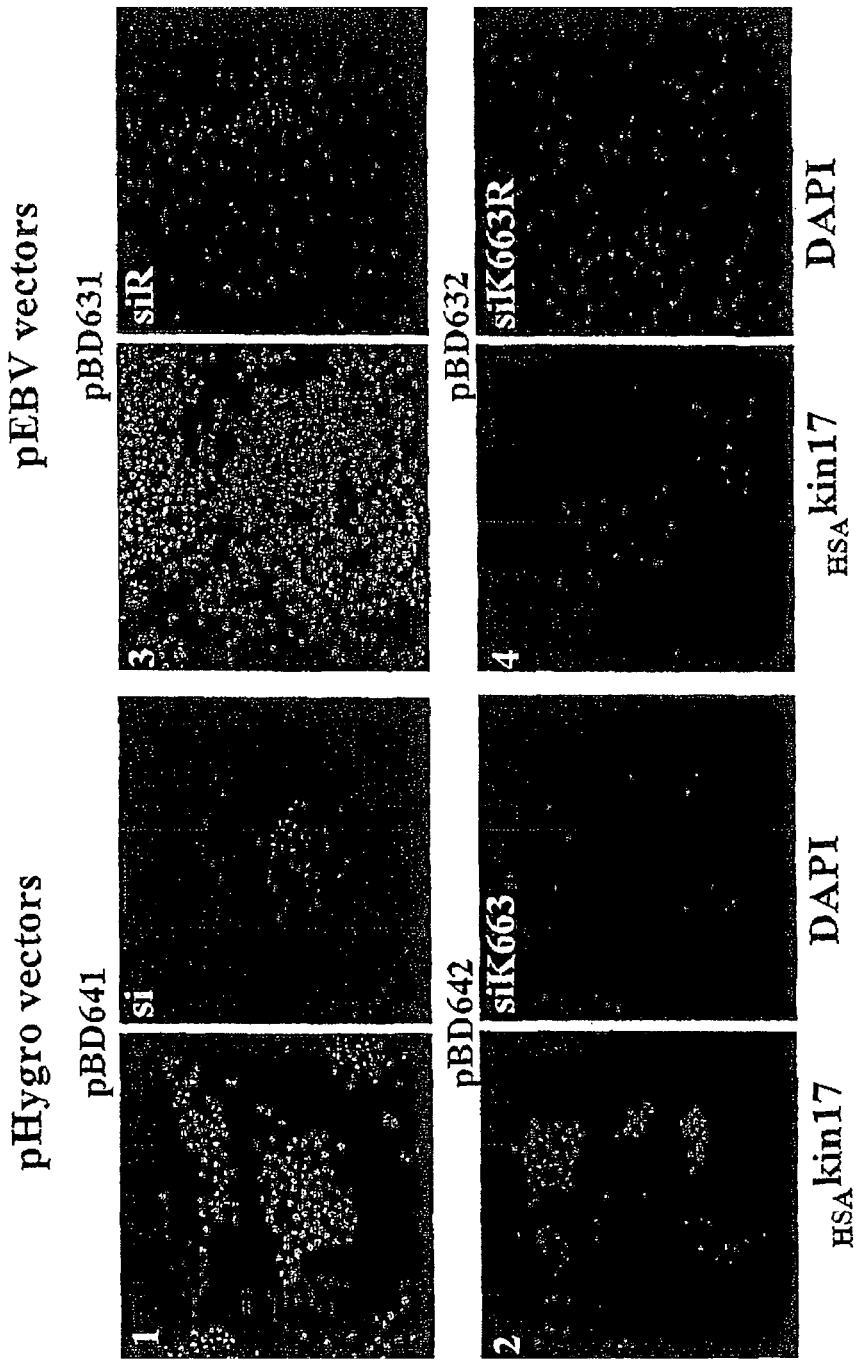

C. Direct cloning: the oligonucleotides encoding an shRNA are introduced directly into the cloning vector pBD751 (pEBVsiR-LacZ') predigested with the Bgl II/Hind III restriction enzymes (FIG. 1C1). The insertion is carried out by replacement of the LacZ' fragment. After ligation and transformation of competent bacteria on an "LB-agar+ampicillin+XGal/IPTG" culture medium, the "white", ampicillin-resistant bacterial clones are selected (FIG. 1C2). Six bacterial clones (or even less) are isolated and amplified, analysis of their plasmid DNA by various enzymatic digestions (for example, Hind III/BamH I) will attest to the cloning efficiency, which is close to 100% (FIG. 1C3). Similarly, vectors carrying puromycin resistance can be obtained from the cloning vector pBD899 (pEBVsiR-LacZ'-Puro). The integrative plasmids are obtained after deletion of the EBV segment (Hpa I/BstE II digestion/Klenow filling and self-ligation) (FIG. 1C4).

FIG. 2: HeLa human cells are cultured and transfected 24 h later, while they are growing exponentially, thereby potentiating the effect of the siRNAs or of the associated vectors. The transfection is carried out with 3 μl of Lipofectamine 2000 (Invitrogen) and either 2 μg of DNA (for the expression vectors) or 60 nM (final concentration) of siRNA duplex. Three days later, the cells are trypsinized and counted and the proteins are analyzed.

Antibodies:
anti-$_{HSA}$kin17: IgK36 and K58 immunoglobulins purified from ascites fluids and corresponding to the monoclonal antibodies mAB K36 and mAB K58 (Biard et al. (58)).
anti-Ku70: Neomarkers, clone N3H10
anti-Ku80: Neomarkers, clone 111
anti-cycline A: Sigma, clone Cy-A1
anti-α tubuline: Sigma, clone B-5-1-2
anti-PCNA: Novo Castra, clone PC10.

FIG. 3: HeLa human cells are transfected with 3 μl of Lipofectamine 2000 (Invitrogen) and either 2 μg of DNA or 60 nM (final concentration) of siRNA duplex. The transfected HeLa cells are cultured in the presence of 250 μg/ml of hygromycin B (Invitrogen) for 3, 10 and 18 days.
1: pEBV-siR (=pBD631)
2: pEBV-siK 663R (=pBD632)
3: pEBV-siK 663D (=pBD664)
4: pEBV-siD (=pBD665)
5: pEBV-si control R (=pBD650).

FIG. 4: 48 h after transfection, RKO cells are seeded at a rate of 5000 cells/cm$^2$ in the presence of hygromycin B (500 μg/ml).

The immunohistochemical detection of the $_{HSA}$kin17 protein is carried out 13 days after transfection (IgG K36; DAPI counterstaining; magnification×50):
1: pHygro-si (pBD641)
2: pHygro-siK 663 (pBD642)
3: pEBV-siR (=pBD631)
4: pEBV-siK 663R (=pBD632).

Figure 5:
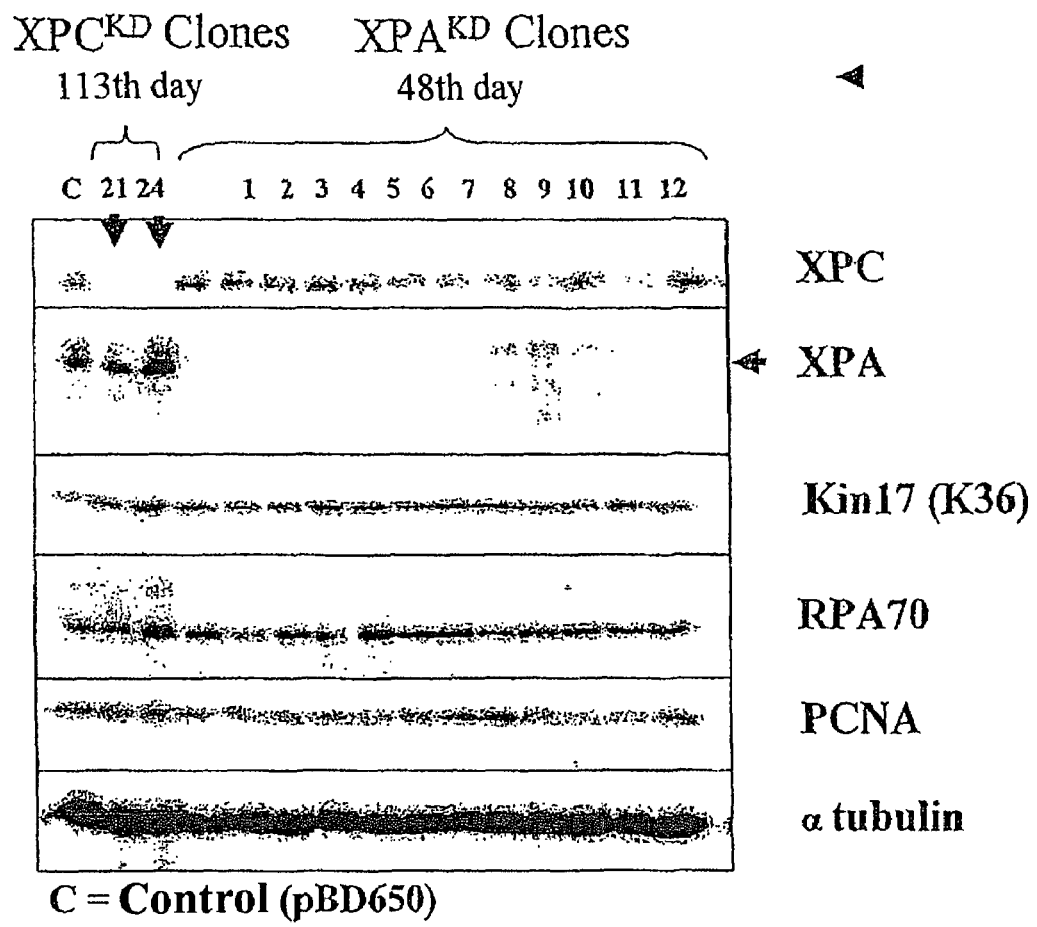

FIG. 5 illustrates the Western blotting analysis of 12 stable XPA$^{KD}$ clones (cellular clones which have become silent—knock down—for XPA) and of two stable XPC$^{KD}$ clones (cellular clones which have become silent—knock down—for XPC).

Antibodies: anti-XPA (Yang Z G et al. (53)) and anti-XPC (Volker M. et al. (54)).

Figure 6:
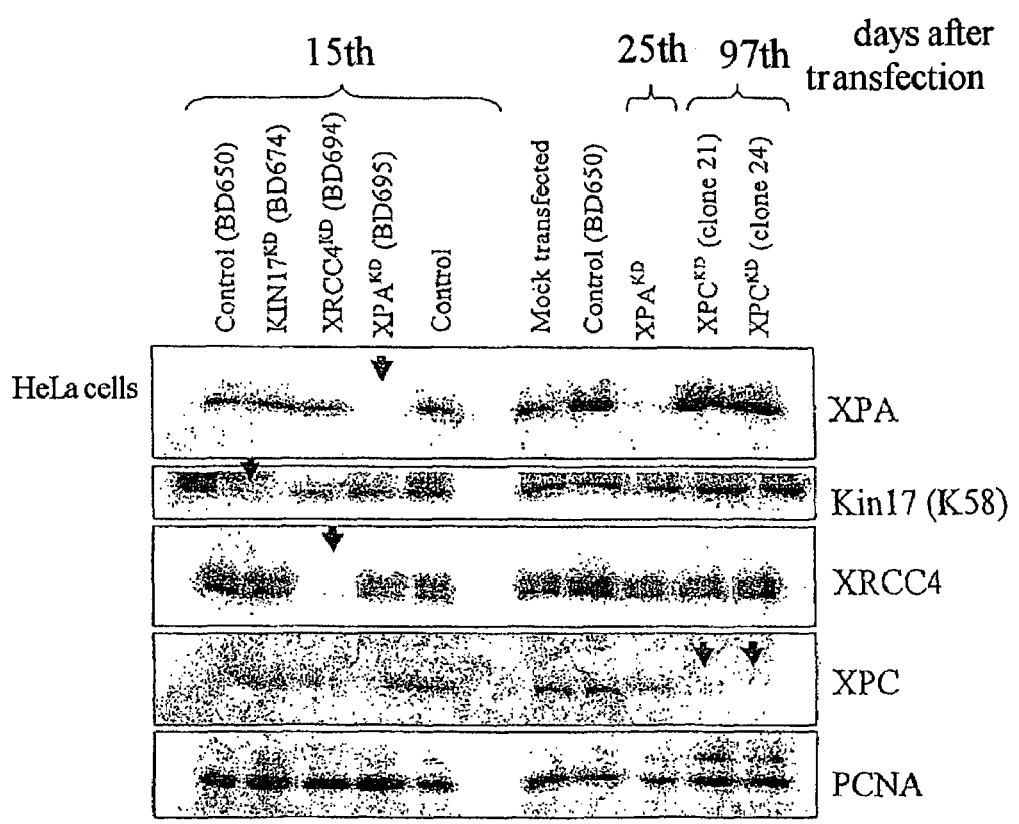

FIG. 6 illustrates the analysis by Western blotting of the extinction of the XPA, XPC, XRCC4 and KIN17 genes in stable populations 15 days after transfection or in established clones. After 15, 25 or 97 days of continuous culture, the cells are trypsinized and counted and the proteins are recovered in 2× Laemmli lysis buffer. The protein equivalent of 100 000 cells is analyzed by Western blotting.

Figure 7:
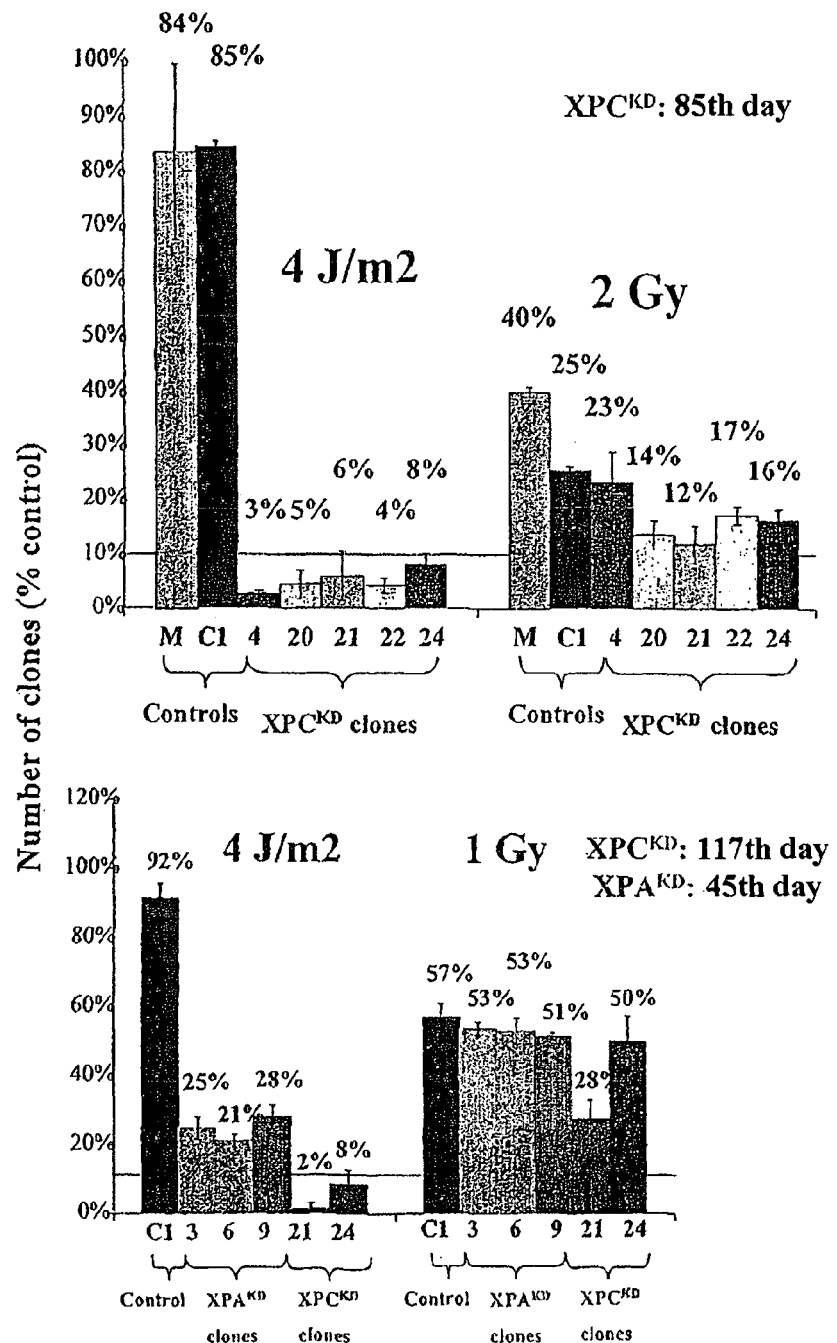

FIG. 7 illustrates the clonogenic growth of various XPA$^{KD}$ and XPC$^{KD}$ HeLa clones after UVC irradiation or ionizing irradiation (γ-rays). 35 cells per cm$^2$ are seeded 24 h before irradiation. The culture is maintained for 14 days in the presence of hygromycin B and the clones are then fixed, stained and counted (only clones of more than 50 cells are taken into account). Each point corresponds to 3 culture dishes (±SD). The XPC$^{KD}$ clones exhibit greater sensibility to UVC than the syngenic XPA$^{KD}$ clones.

Figure 8:
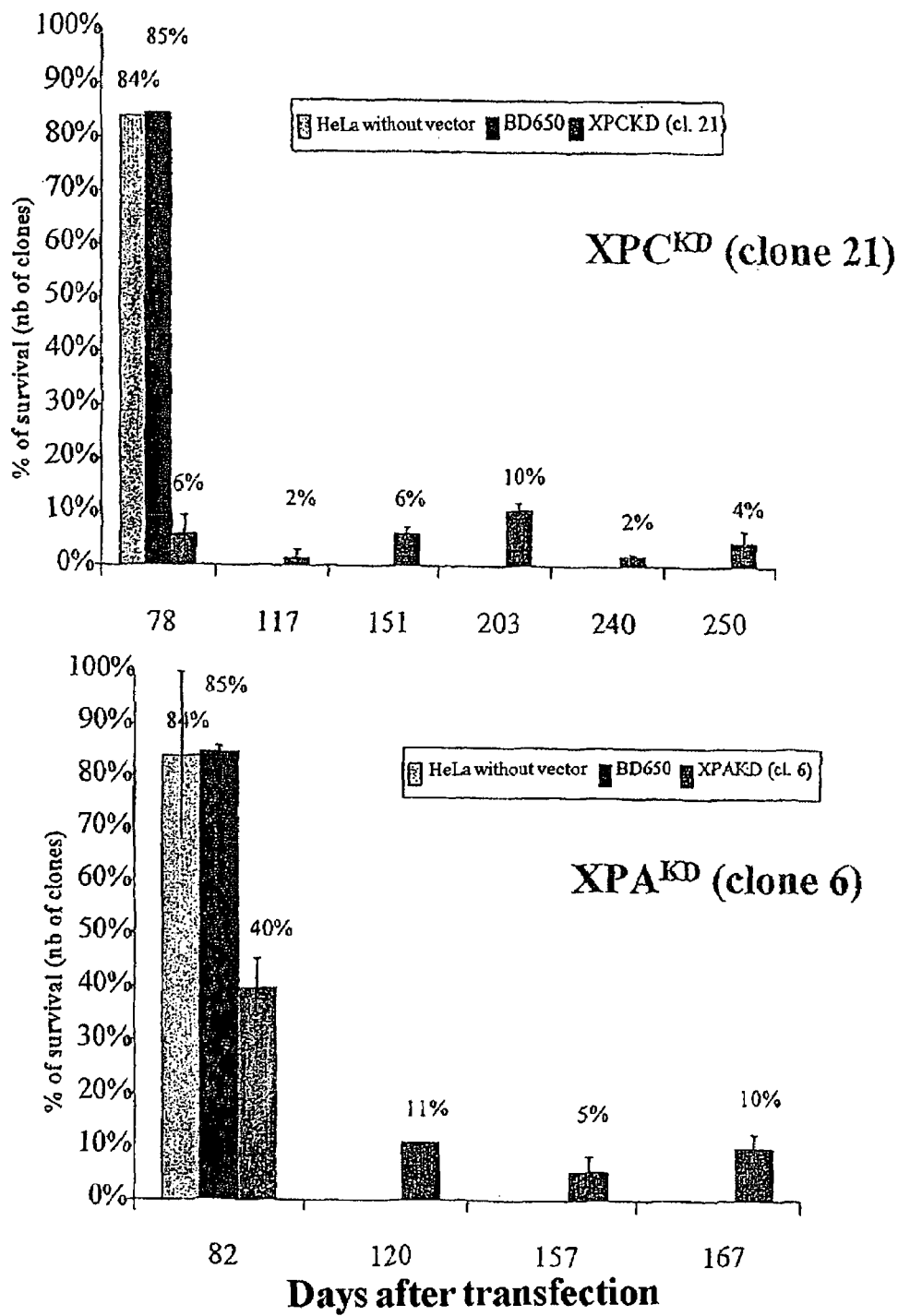

FIG. 8 illustrates the monitoring of the stability over time of the XPA$^{KD}$ and XPC$^{KD}$ HeLa clones with respect to their sensibility to UVC rays. At various times after transfection and continuous culture, the cells are trypsinized, placed in culture, irradiated and analyzed according to the criteria of a clonogenic growth as described in the legend of FIG. 7.

Figure 9:
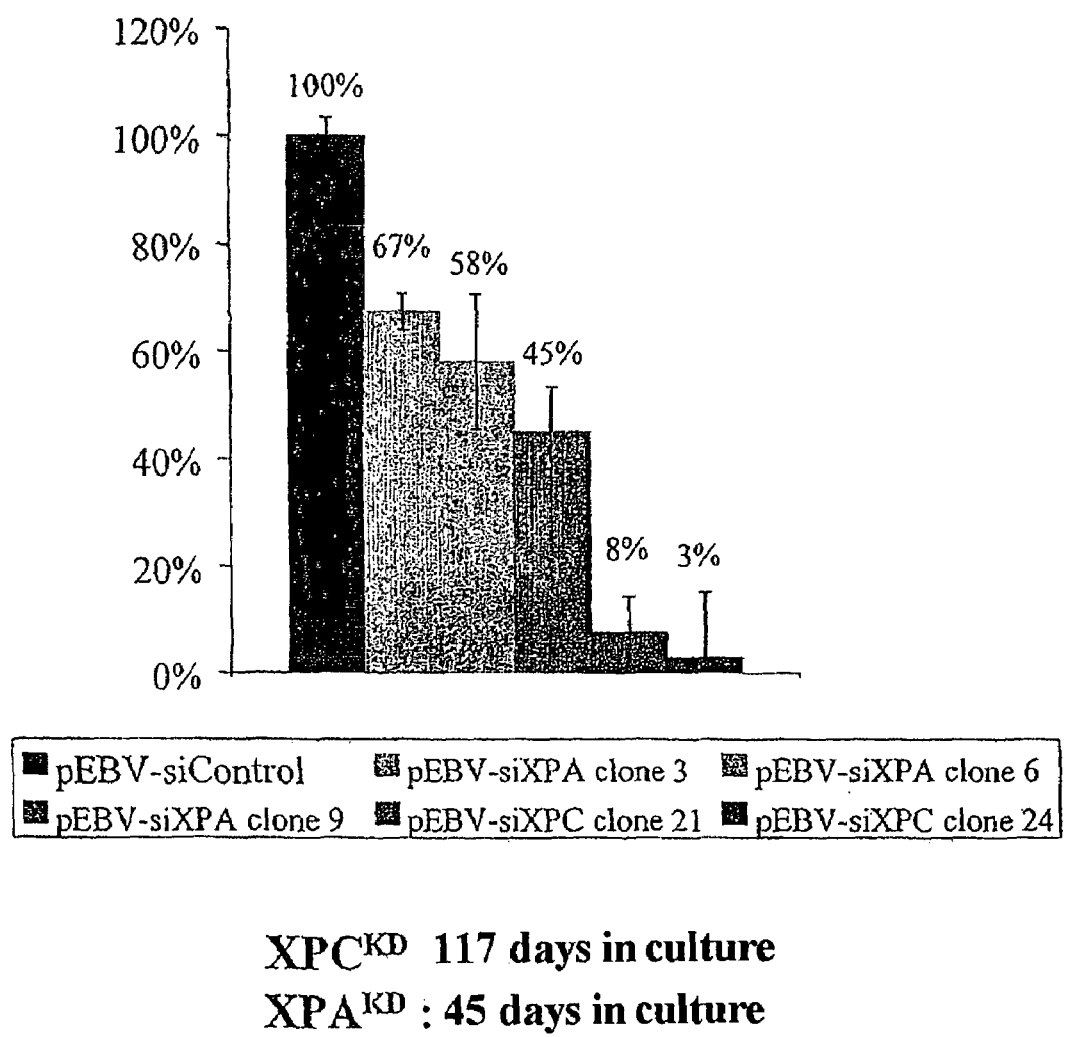

FIG. 9 illustrates the difference in plating efficiency of the XPC$^{KD}$ HeLa clones compared with the XPA$^{KD}$ clones or with the control cells and reflects the very considerable spontaneous difficulties in growth. At various times after transfection and continuous culture, the cells are trypsinized, placed in culture and analyzed according to the criteria of a clonogenic growth as described in the legend of FIG. 7.

Figure 10:
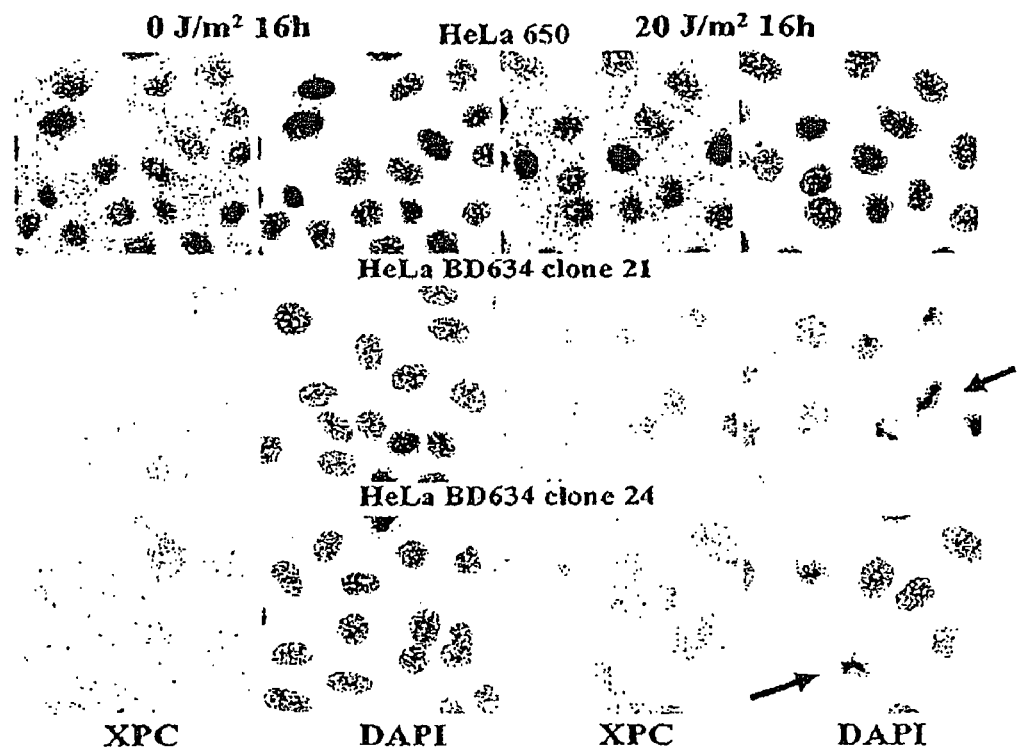

FIG. 10 illustrates the fact that the loss of expression of the XPC gene is associated with a high genomic instability. The XPA$^{KD}$, XPC$^{KD}$ cells and the control cells are placed in culture at the same density and irradiated at 20 J/m$^2$ (UVC). 16 h later, the cells are fixed with 4% paraformaldehyde (20 min) and permeabilized with 0.5% Triton×100 (5 min). The cells are then labeled for XPC (or XPA, not shown here) and counterstained with DAPI (DNA-specific labeling). The almost complete extinction of the expression of the XPC gene is confirmed in two XPC$^{KD}$ clones (clones 21 and 24). Furthermore, the appearance of numerous apoptotic figures is demonstrated by the DAPI staining (arrow on the right panels).

Figure 11:
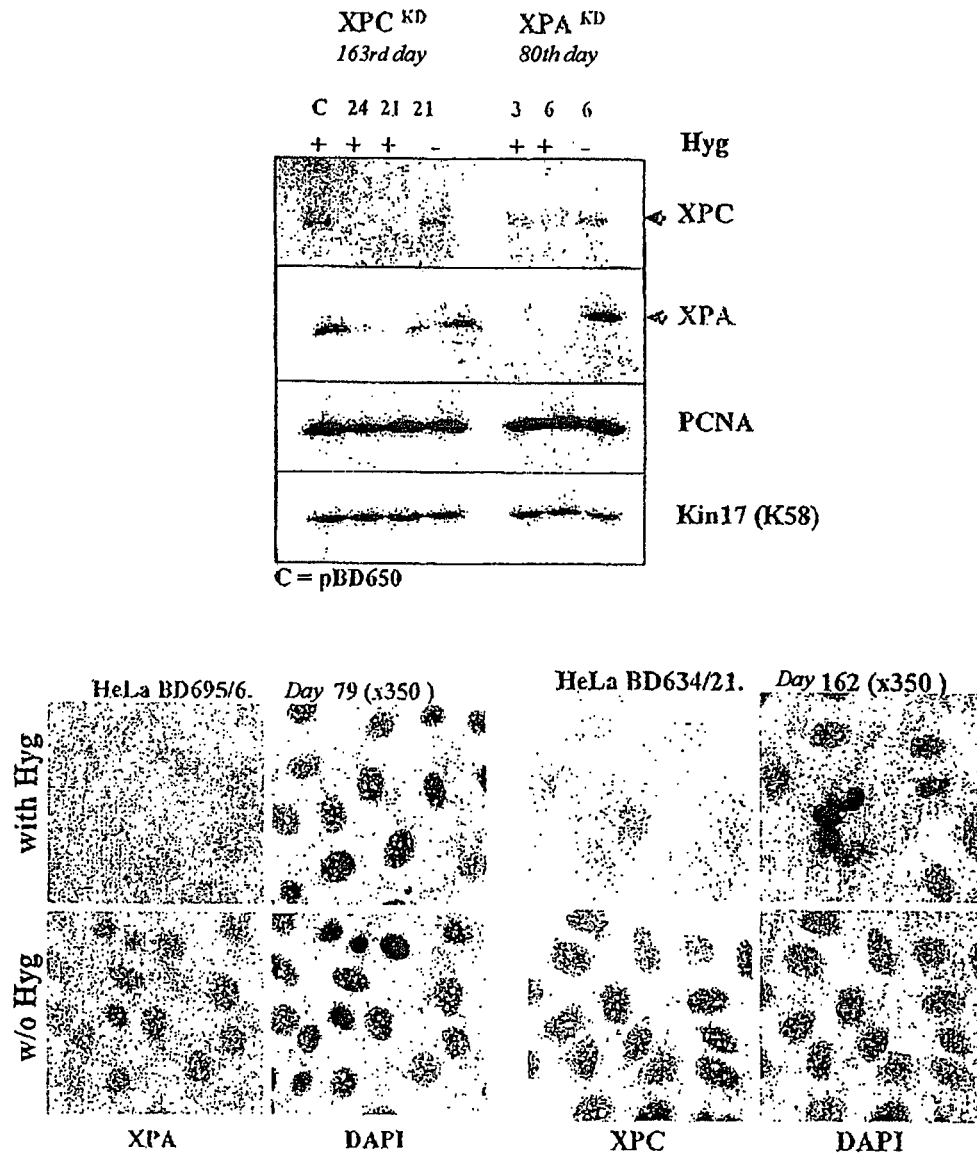

FIG. 11: Demonstration of the reversibility of the system used by recovery of the gene rendered silent (XPA or XPC). The clones stable for 163 days (XPC$^{KD}$) and 80 days (XPA$^{KD}$) are cultured for 10 days in the presence or absence of the selectable marker M2 (hygromycin B). The cells are then analyzed by Western blotting or immunocytochemical labeling. A reappearance of the expression of the XPC or XPA genes is observed in 100% of the cells; thereby attesting to a complete reversion of the phenotype which had been imposed for several months by the pEBV-siRNA vectors, according to the invention.

Figure 12:
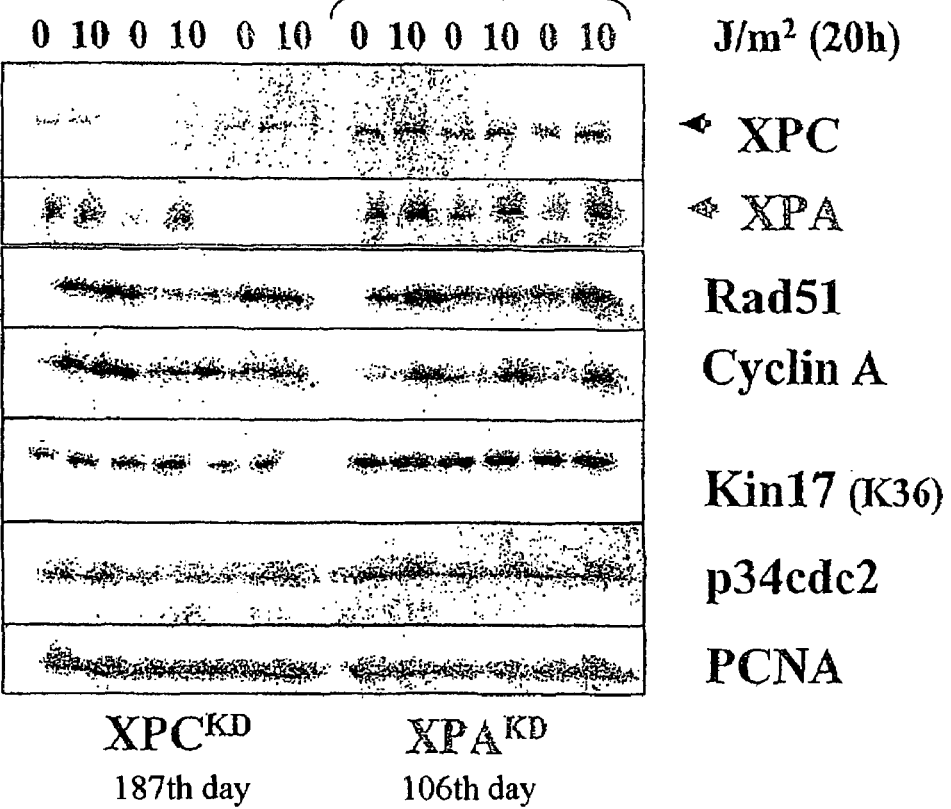

FIG. 12: Further demonstration of the reversibility of the system used by recovery of the gene rendered silent (XPA or XPC). Under conditions identical to those of FIG. 11 and in a completely independent experiment, complete reversion of the phenotype is also observed.

Figure 13:
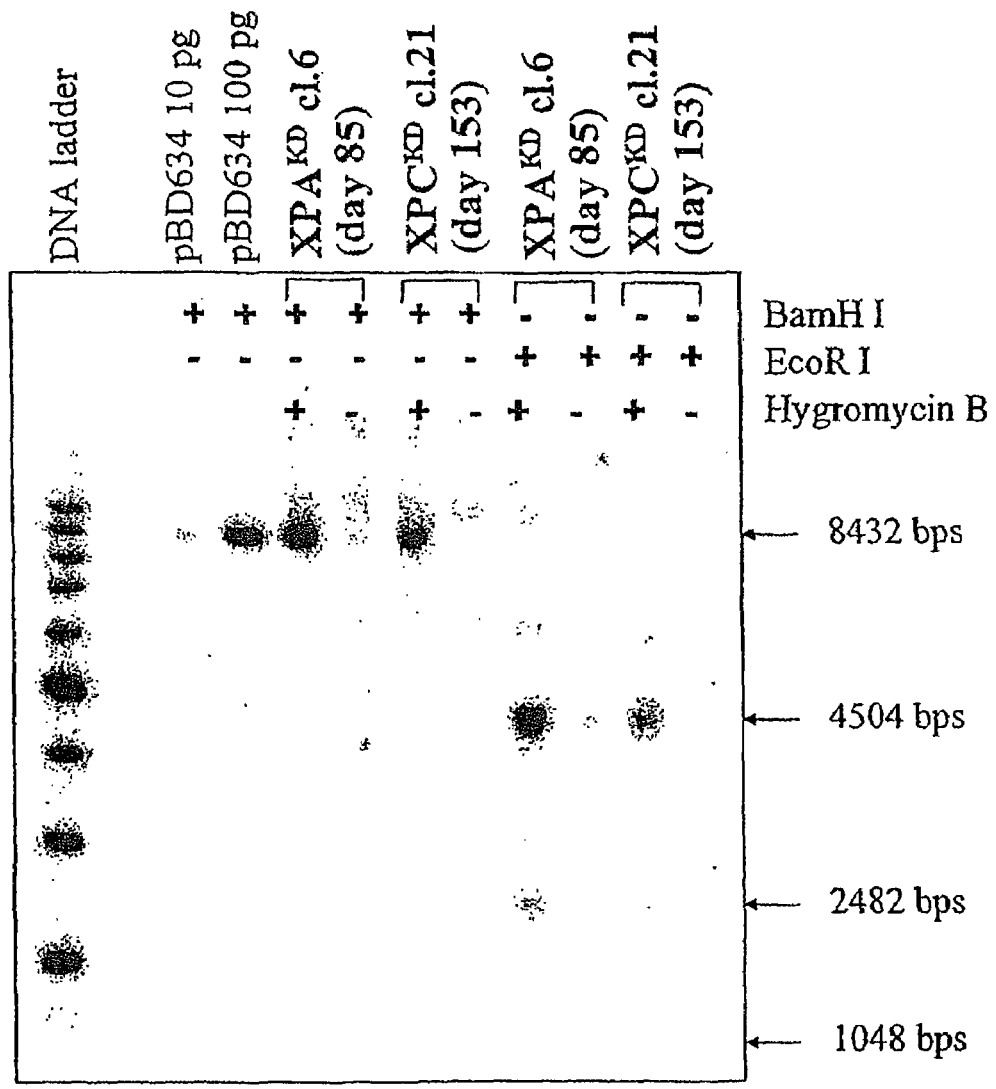

FIG. 13: Complete loss of the pEBV-siRNA vectors according to the invention 10 days after the elimination of hygromycin B from the culture medium. After culturing for 10 days in the presence or absence of hygromycin B, the total DNA (genomic+episomal) is isolated from the XPA$^{KD}$ and XPC$^{KD}$ clones. 10 μg are then analyzed by Southern blotting. The probe used corresponds to the entire pBD634 vector, linearized and labeled with $^{32}$P by random priming (Amersham). The following points are observed: (1) in the XPC$^{KD}$ and XPA$^{KD}$ clones the pEBV-siRNA vectors are maintained in an episomal form, (2) with a low copy number per cell (approximately 10-20). (3) The absence of hygromycin B leads to a rapid and complete loss of these vectors.

Figure 14:
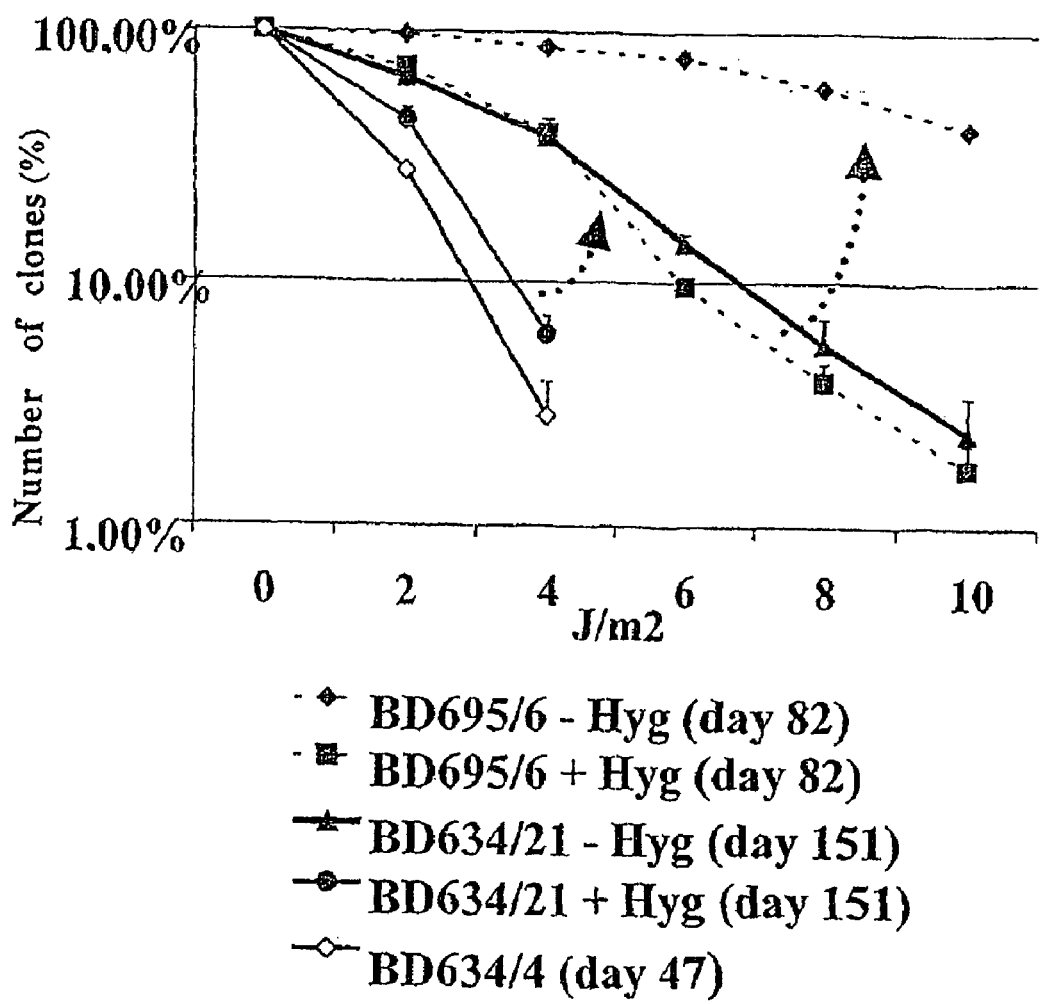

FIG. 14 (clonogenic growth of HeLa cells): The complete reversion of the expression of the XPA$^{KD}$ and XPC genes is not always associated with complete recovery of a characteristic phenotype (sensitive to UVC): demonstration of effects collateral to the loss of expression of the XPC gene for several months. The cells are trypsinized, placed in culture, irradiated and analyzed according to the criteria of a clonogenic growth as described in the legend of FIG. 7. The culturing is carried out with or without hygromycin B. It is noted that the reverted XPA$^{KD}$ cells return to a normal sensitivity to UVC, whereas the XPC$^{KD}$ cells remain very sensitive to UVC, although they have returned to their normal content of XPC protein. This demonstrates the fact that the absence of the XPC protein for several months has led to genetic damage that could not be envisioned at the start.

Figure 15:
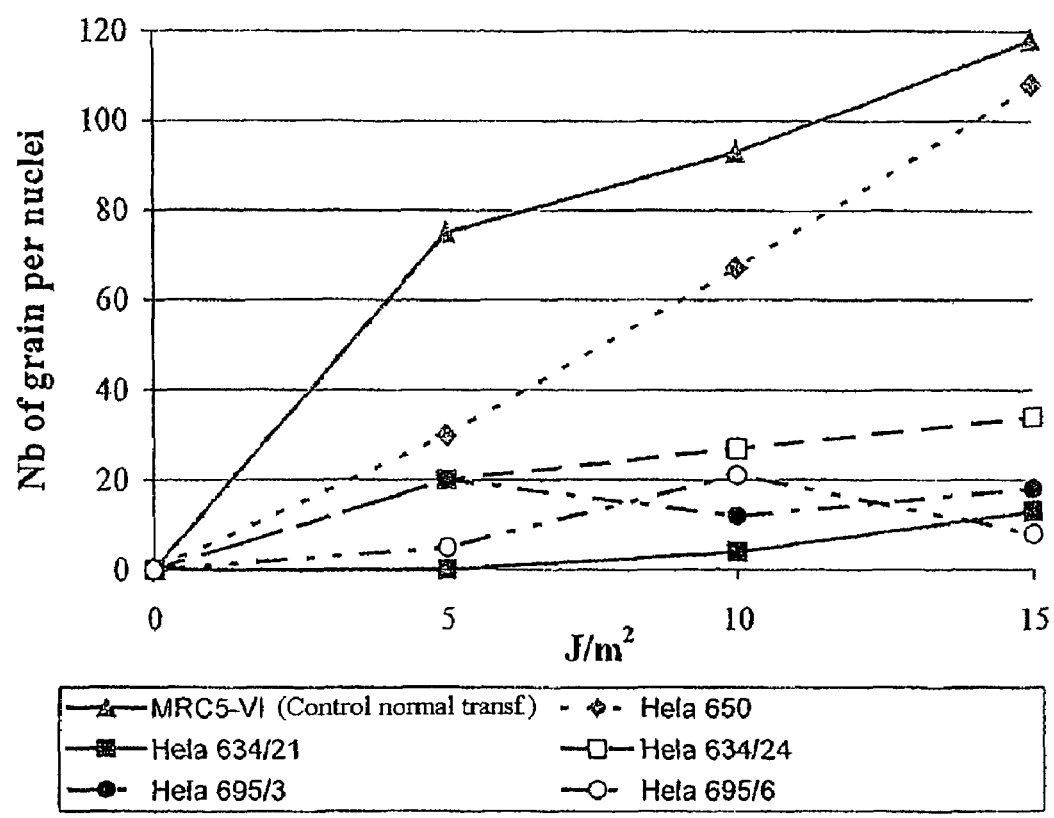

FIG. 15: Deficient DNA repair (UDS or unscheduled DNA synthesis) after UVC irradiation in XPA$^{KD}$ and XPC$^{KD}$ HeLa clones. The XPA$^{KD}$ (clones 3 and 6) and XPC$^{KD}$ (clones 21 and 24) cells are placed in culture on a glass coverslip and the DNA repair after UC irradiation is monitored by incorporation of [$^3$H] thymidine as previously described (Sarasin et al. (55)).

Figure 16:
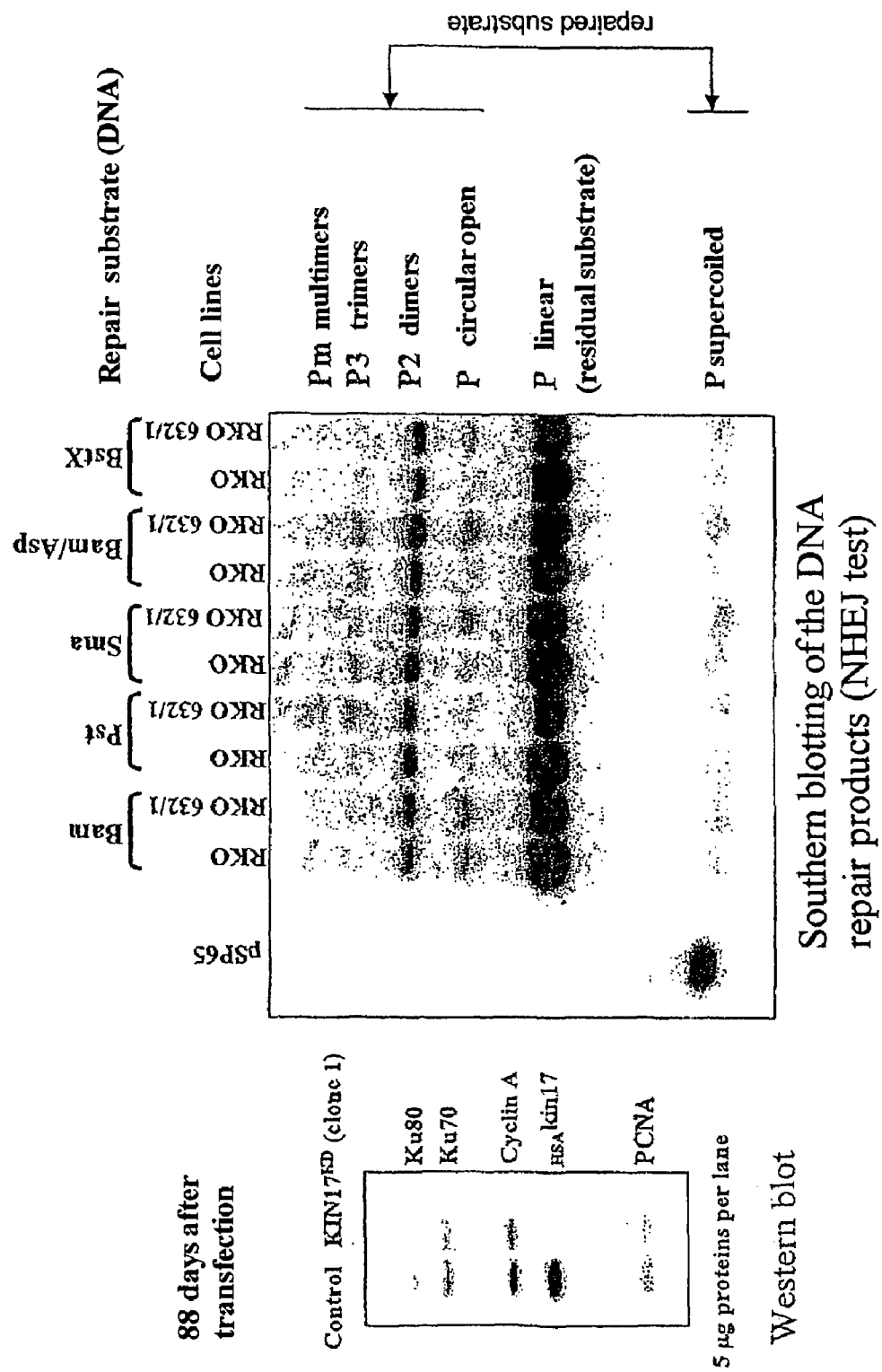

FIG. 16: Activity of NHEJ (nonhomologous end joining) repair of a KIN17$^{KD}$ clone in culture for 88 days. According to a protocol adapted from Daza et al. (56), protein extracts which conserve an NHEJ activity are prepared from a stable clone no longer expressing the kin17 protein using a vector according to the invention. In an in vitro repair test, linearized plasmid vectors called Bam, Pst, Sma, Bam/Asp and BstX and which have blunt, 5'-protruding or 3'-protruding ends are analyzed by Southern blotting in order to note the repair thereof (recircularization). The characteristic DNA bands are observed on the right of the figure, where "P linear" corresponds to the residual product and all the other bands to the repaired product. In this test, a slightly greater DNA repair is observed in an RKO clone deficient in kin17 protein.

Figure 17:
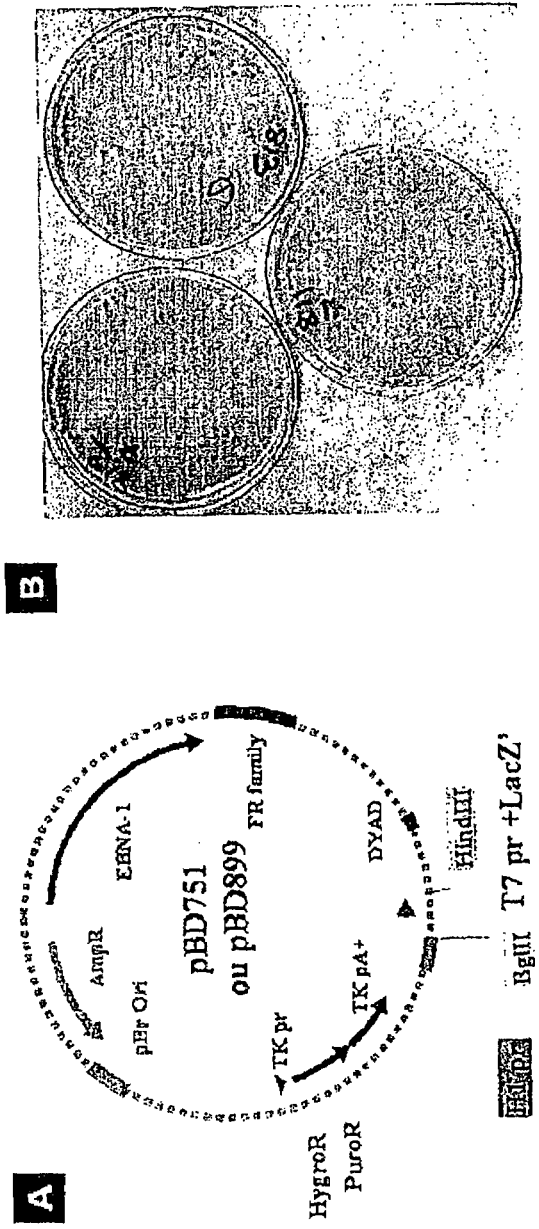
Figure 17:
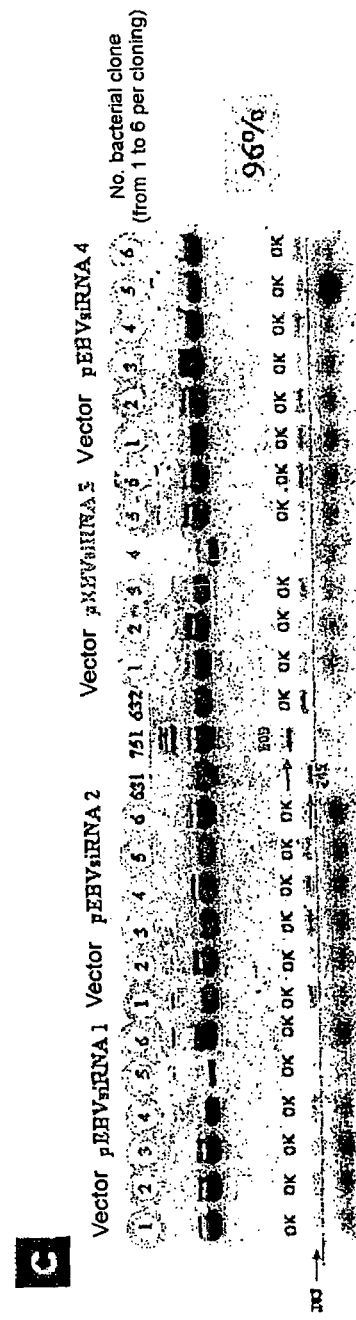

FIG. 17: Selection of recombinant vectors. (A): representation of the cloning vector (intermediate product for the preparation of a vector according to the invention) pBD751 (pEBV-LacZ'-hygro). (B): LB-agar plates on which blue or white bacteria have grown; selecting the white colonies (6 or 7 are preselected). The colonies selected are those which carry the recombinant vectors, the LacZ' sequence bordered by the BglII/HindIII sites being replaced with the shRNA sequences of 64 nucleotides which are synthesized and are characteristic of a target gene. (C): analysis of four clonings (vector pEBVsiRNA 1 to 4) for which 6 bacterial clones were randomly selected. These clones were amplified on the day in liquid culture (LB+ampicillin) and their DNA was purified according to conventional molecular biology techniques (DNA minipreparation). The DNA of each clone was digested with the two restriction enzymes HindIII/BamHI for 1 h at 37° C. The analysis on an agarose gel (1.5%) shows a cloning efficiency close to 100%. The recombinant clones are identified in the following way: HindIII/BamHI restriction digestion is, from the pBD751 cloning vector, a fragment of 509 nucleotides (corresponding to the T7-LacZ' sequences); if the vector recircularizes, a fragment of 245 nucleotides will be obtained, as for the empty pBD631 vector; on the other hand, if the insert (shRNA sequence) is correctly integrated, a fragment of 303 nucleotides will be obtained (as for the pBD632 vector already cloned). In the present case, it is noted that 23 of the 24 clones exhibit a perfect digestion profile.

Figure 18:
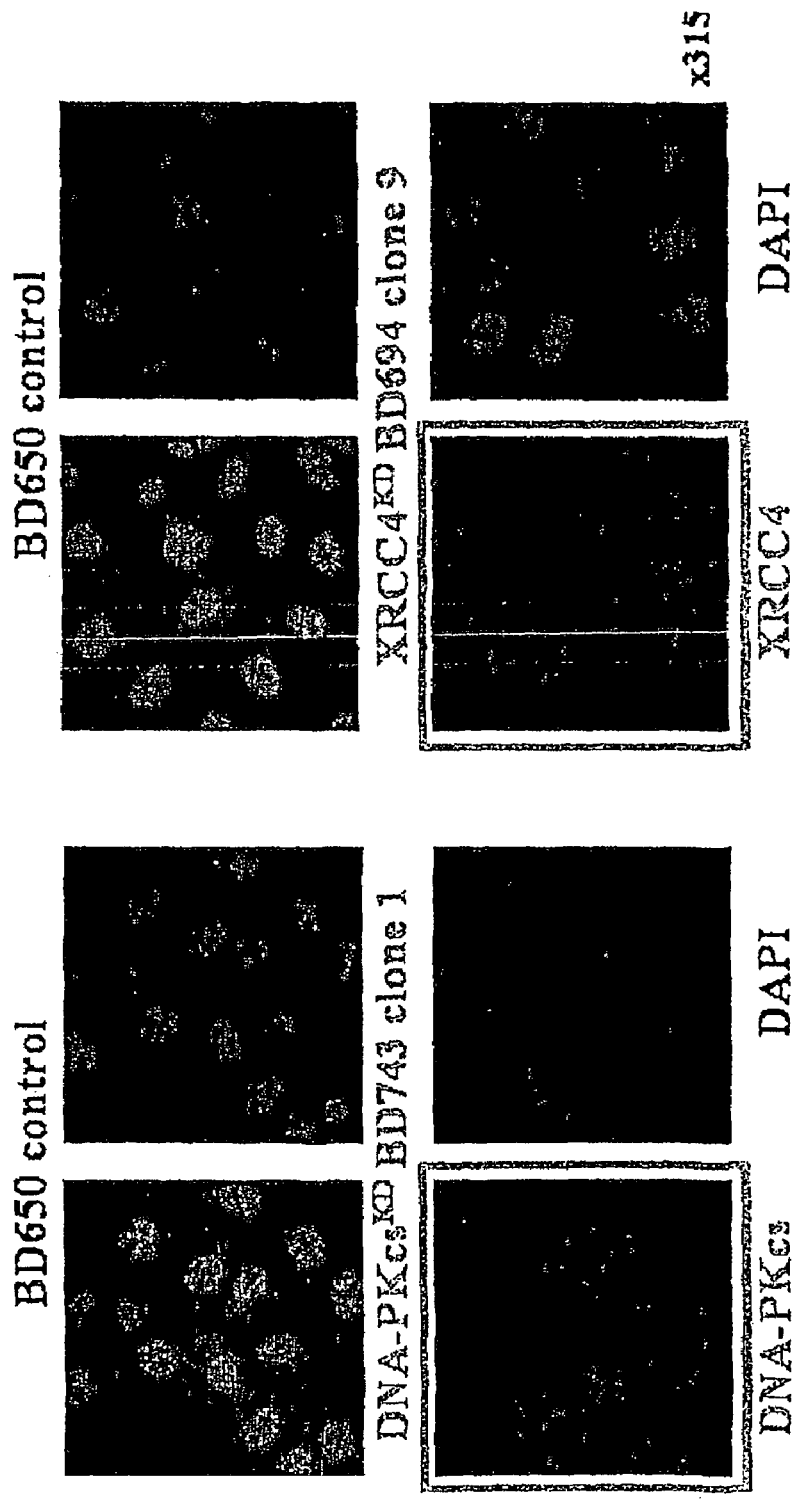

FIG. 18: 48 h after transfection of the HeLa cells with either a pBD743 vector or a pBD694 vector, under the conditions disclosed above, the HeLa cells are plated at a rate of 5000 cells/cm², in the presence of hygromycin (250 µg/ml). Detection of the DNA-PKcs and XRCC4 proteins is carried out by Western blotting 40 days after transfection (anti-DNA PKcs antibody LabVision Neomarker #MS-423-PABX; anti-XRCC4 antibody Abcam clone ab145). An extinction of the DNA-PKcs and XRCC4 genes is observed: the two vectors are effective for extinguishing the DNA-PKcs (pBD743 vector) and XRCC4 (pBD694 vector) genes.

Figure 19:
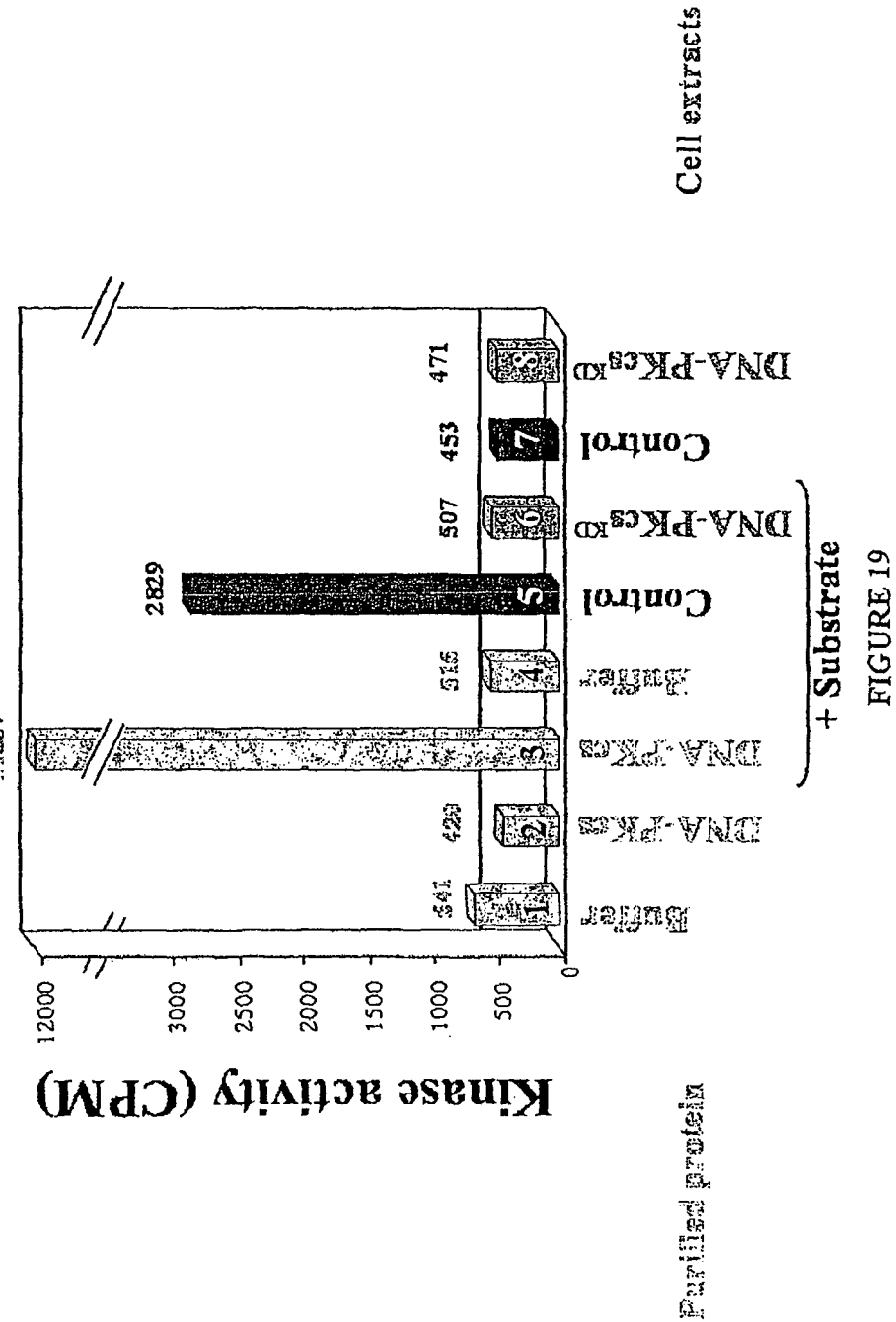

FIG. 19: Analysis of the activity of a clone silent for the DNA-PKcs gene (clone BD743.1 or DNA-PKcs$^{KD}$, for knock-out). A test for DNA PKcs activity (pull-down assay) was accomplished according to the protocol already published by Finnie et al. (*Proc. Natl. Acad. Sci. USA*, 92, 320-324, 1995). Briefly, the DNA-binding proteins are isolated on 5 mg of cellulose resin+double-stranded DNA (Amersham), and the DNA PKcs activity is tested by the incorporation of [γ-$^{32}$P] ATP on 4 nmol of a substrate specific for DNA PKcs (Promega). The incorporation of radioactive ATP into the substrate is measured by liquid scintillation. Lanes 1 to 4 and 7 and 8 correspond to the various controls.

(1) Buffer alone without any protein or substrate (this is the radioactive background noise of the technique).

(2) 50 U of purified DNA-PKcs protein (Promega) without substrate.

(3) 50 U of purified DNA-PKcs protein (Promega) with substrate (this is the positive control).

(4) Buffer without protein but with substrate.

(5) 25 µg of cell extract of a control line (carrying the pBD650 vector) with substrate (this is the basal level of the DNA-PKcs activity in HeLa cells).

(6) 25 µg of cell extract of the BD743.1 clone (DNA PKcs knock down) with substrate (this is the level of residual activity of the silent clone: it lies at the level of the background noise of the technique).

(7) 25 µg of cell extract of a control line (carrying the pBD650 vector) without substrate (negative control).

(8) 25 µg of cell extract of the BD743.1 clone (DNA PKcs knock down) without substrate (negative control).

After more than 100 days of culture, the activity of the enzyme is completely absent (compared with the background noise intrinsic to the technique used).

Figure 20:
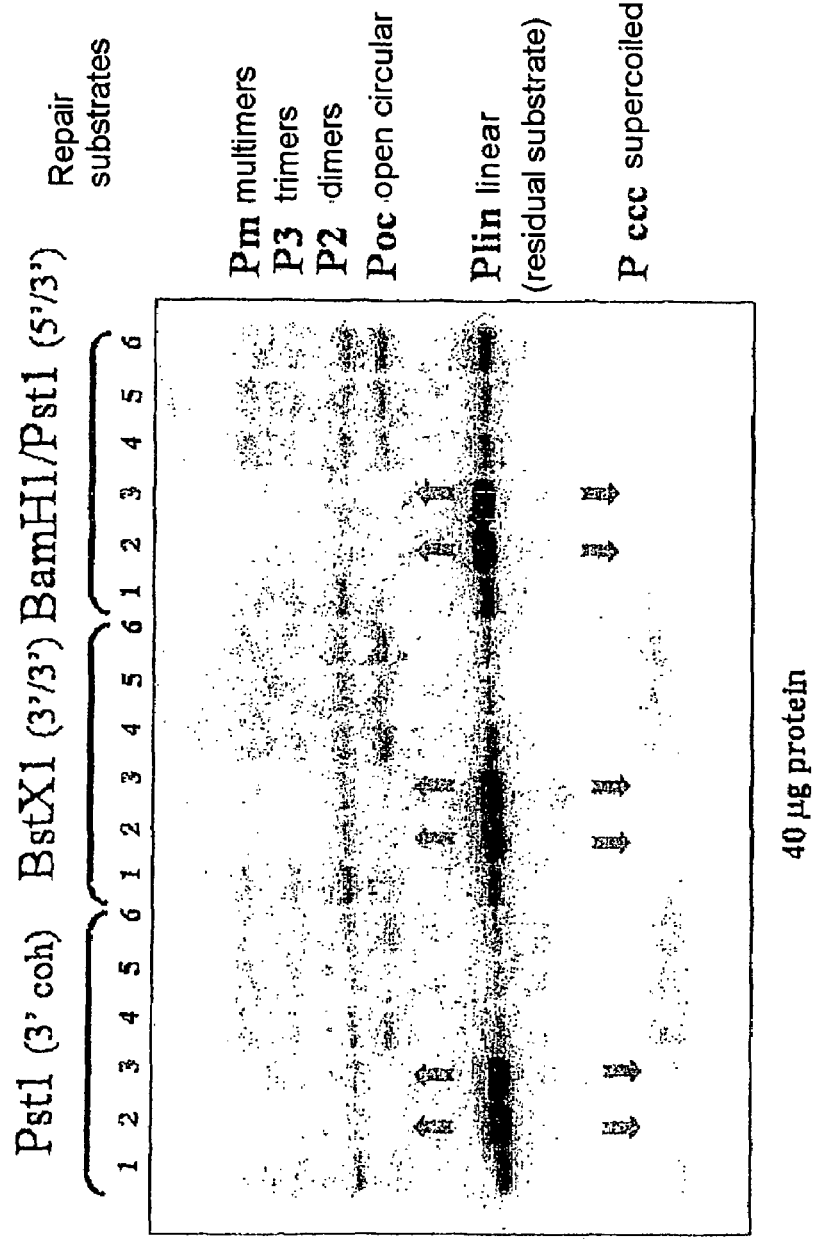

FIG. 20: Activity of NHEJ (nonhomologous end joining) repair of an XRCC4$^{KD}$ and DNA PKcs$^{KD}$ clone after 75 days of culture. According to the protocol described in FIG. 16 and adapted from Daza et al. (56), protein extracts which conserve an NHEJ activity are prepared from stable clones carrying a vector according to the invention. In an in vitro repair test, linearized plasmid vectors called Bam, Pst, Sma, Bam/Asp and BstX and which have blunt, 5'-protruding or 3'-protruding ends are analyzed by Southern blotting in order to note their repair (recircularization). The characteristic DNA bands are observed on the right of the figure, where "P lin" corresponds to the residual product ("linear product") and all the other bands to the repaired products (Pccc for "supercoiled circular product"; Poc for "circular product open on one strand", P2, P3 and Pm for multimers). As shown by the arrows, it is noted that repair is completely absent in the XRCC4$^{KD}$ clone (clone 9) irrespective of the substrate used (well 2 for each substrate) and repair is greatly altered for the DNA PKcs$^{KD}$ clone (clone 1) (well 3 for each substrate). Conversely, the various other KIN17$^{KD}$ silent clones do not show any variation compared with the control line carrying the pBD650 vector.

FIGS. 18-20 confirm the advantage of the vectors according to the invention in showing the long-term extinction of the DNA-PKcs and XRCC4 proteins, associated with the loss of their main activity in DNA repair (NHEJ recombination).

Figure 21:
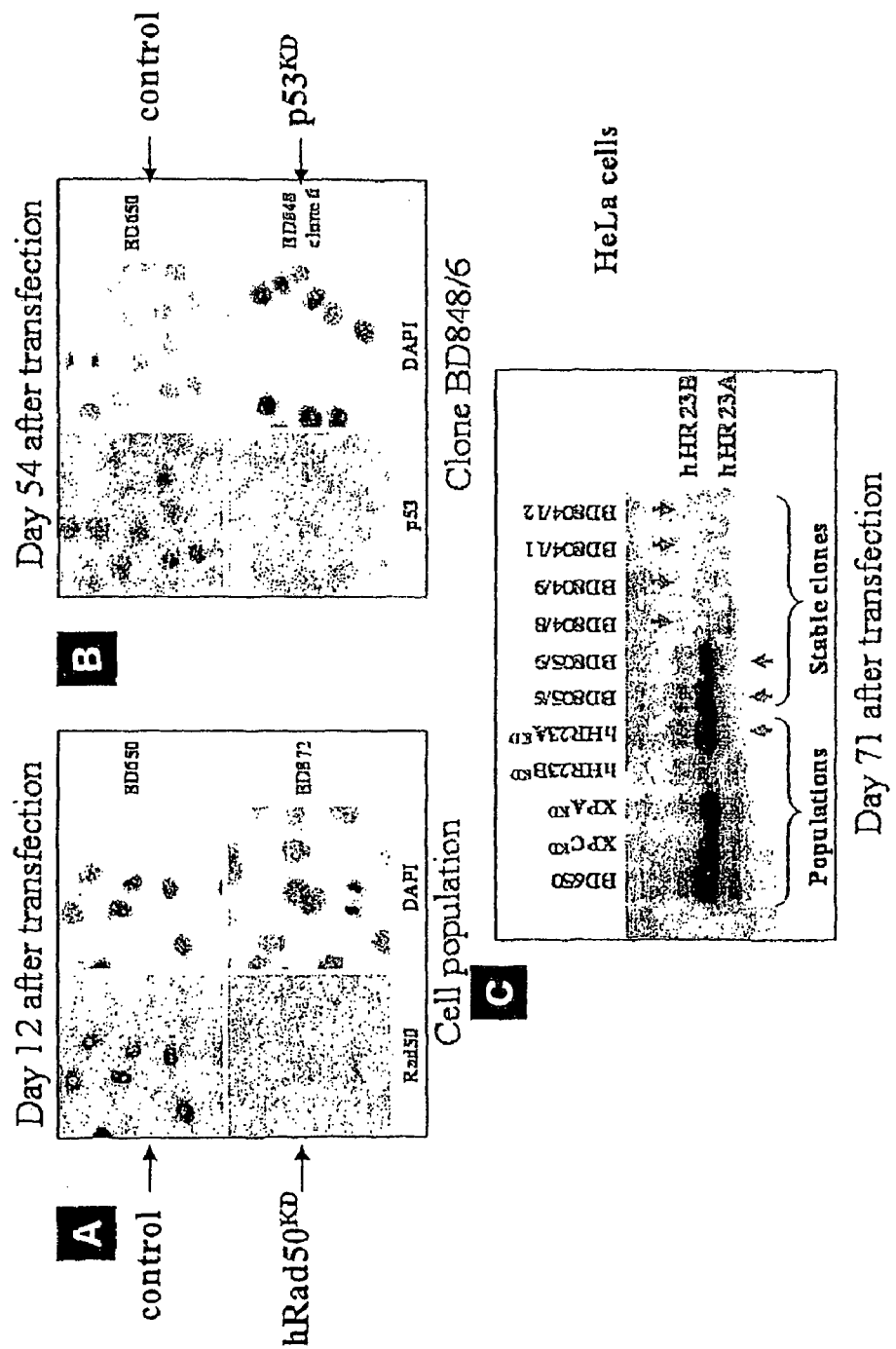
Figure 22:
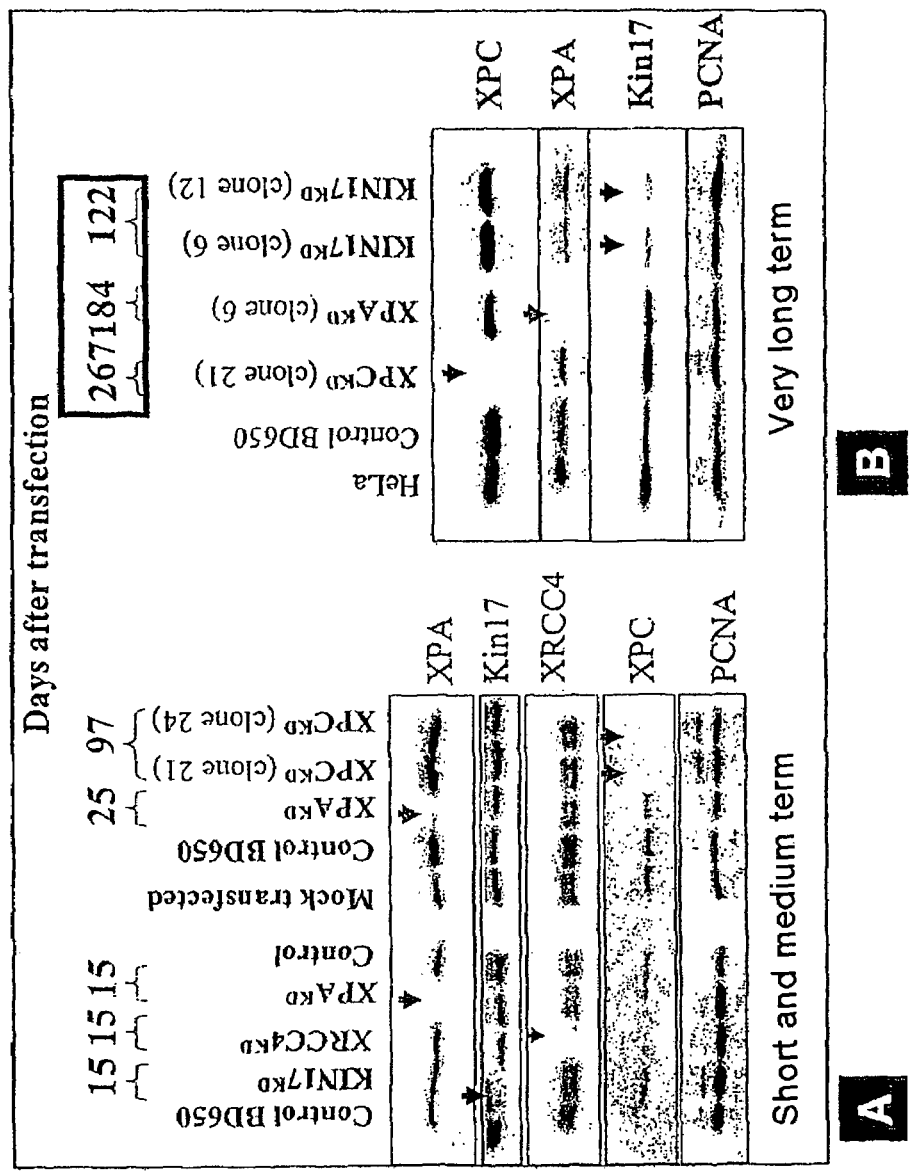

FIG. 21: Analysis of the proteins by immunocyto-chemistry (A and B) or by Western blotting (C) after extinction of the hRad50, p53, hHR23A and hHR23B genes in HeLa cells. The HeLa cells were transfected with the vectors in accordance with the invention: pBD872, pBD848, pBD804 and pBD805 vector. Two days after transfection, the HeLa cells are cultured in the presence of hygromycin B (250 µg/ml) and analyzed at the various times indicated, according to the protocols previously described. (A): Immunocytochemical labeling for the hRad50 protein (Calbiochem antibody #552140). HeLa population carrying the pBD872 vector directed against hRad50 for 12 days. (B): Immunocytochemical labeling for the p53 protein (antibody DO-7 hybridoma supernatant). HeLa clone carrying the pBD848 vector directed against p53 for 54 days. (C) Western blotting for the hHR23A and hHR23B proteins (antibodies generously donated by Dr Kaoru Sugasawa, Ph.D., Cellular Physiology Laboratory, RIKEN Discovery Research Institute, 2-1 Hirosawa, Wako, Saitama 351-0198, Japan). Cell populations and clones carrying the pBD804 and pBD805 vectors, respectively directed against hHR23B and hHR23A, for 71 days;

FIG. 22: Analysis of the proteins by Western blotting showing the short-term and medium-term (A) or long-term (B) effectiveness of the vectors according to the invention in HeLa cells. Example of extinction of the expression of the XPA (pBD695 vector), XPC (pBD634), XRCC4 (pBD694) and KIN17 (pBD674) genes after transfection of HeLa cells and culture in the presence of hygromycin B (250 µg/ml): for each gene targeted, from 2 to 4 vectors carrying different shRNA sequences are constructed. Other results, not represented, show that the clones in culture are stable for long periods: XRCC4: >120 days, DNA-PKcs: >130 days, XPA: >390 days, Kin17: >1 year, hHR23B: >150 days, hHR23A: >150 days, p53: >60 days, XPC: >390 days.

LIST OF SEQUENCES OF THE APPLICATION

| No. of sequences | |
| --- | --- |
| 1 | H1 promoter |
| 2 | H1 sense primer |
| 3 | H1 antisense primer |
| 4 | siRNA kin17 |
| 5 | siRNA XPC |
| 6 | siRNA XPA |
| 7 | siRNA XRCC4 |
| 8 | siRNA Ku70 |
| 9 | siRNA DNA-PK |
| 10 | siRNA Rad50 |
| 11 | siRNA Rad51 |
| 12 | siRNA Rad52 |
| 13 | siRNA HR23B |
| 14 | siRNA HR23A |
| 15 | siRNA p53 |
| 16 | pBD751 sense primer |
| 17 | pBD751 antisense primer |
| 18 | oligo1-siKin17R663 |
| 19 | oligo2-siKin17R663 |

It should be clearly understood, however, that these examples are given only by way of illustration of the subject matter of the invention, of which they in no way constitute a limitation.

Example 1

Cloning of the Various Vectors shRNA Sequences

The shRNA sequences contain two identical 19-nucleotide motifs in reverse orientations, separated by a spacer arm of 9 bp of nonhomologous sequences (TTCAAGAGA or any other sequence). A cloning site for the Bgl II (or other) restriction enzyme, followed by a transcription start sequence (generally CCG), is introduced 5' of this "sense" oligonucleotide. A fragment of 6 thymidines, which constitutes a termination signal for RNA Pol III, is introduced 5' of the "antisense" oligonucleotide. A Hind III (or other) cloning site is introduced at the 3' end of the shRNA sequences.

FIG. 1 illustrates such a construct for an siRNA designed against the mRNA of the KIN17 gene and corresponds to positions 663-681 (siK663/kin17), with reference to the sequence accessible under Genbank accession number NM_012311.

Cloning Strategy

The cloning strategy with an oligodeoxynucleotide (Eurogentec, Belgium) is also illustrated in FIG. 1A. The sense and antisense oligodeoxynucleotides are hybridized in such as way as to form a double-stranded DNA with protruding Bgl II and Hind III ends in the following way: the oligodeoxynucleotides are taken up in autoclaved sterile water (nuclease-free) at the concentration of 3 mg/ml. 1 µl of each oligodeoxynucleotide (at 3 mg/ml) is removed and 48 µl of buffer (100 mM NaCl; 50 mM Tris, pH 7.5) are added. The pairing is carried out in a thermocycler (PCR machine of undetermined brand) according to the following program: 95° C. for 5 min, then 5 min at the following temperatures: 90° C., 85° C., 80° C., 75° C. and 70° C. This is followed by the temperature being maintained at 37° C. for 30 min and at 4° C. until the samples are recovered. The paired oligodeoxynucleotides are then stored at −20° C. until the cloning.

H1 RNA Promoter

To clone the H1 RNA promoter into the pSUPER vector, the following PCR primers (Brummelkamp et al. 2002 (5)) were used:

(SEQ ID NO: 2)
Sense:
5'-CCATGGAATTCGAACGCTGACGTC-3' and (SEQ ID NO: 3)
Antisense:
5'-GCAAGCTTAGATCTGTGGTCTCATACAGAACTTATAAGATTCCC-3'.

Direct cloning of the paired oligonucleotides (encoding an shRNA) is obtained using the pBD751 (pEBVsiR-LacZ') or pBD899 (pEBVsiR-LacZ'-Puro) vectors as described in FIG. 1C. The pBD631 (pEBVsiR) vector, pBD884 (pEBVsiR-Puro) vector or pBD665 vector (pEBVsiD; vector carrying the siRNA cassette in the sense opposite to that of the pBD631 vector) can also be used.

Similarly, indirect cloning can be undertaken after introduction of the paired oligonucleotides into the PSUPER vector and then recovery of the siRNA cassette (H1 promoter+shRNA) by Kpn I/BamH I digestion (New England Biolabs). This siRNA cassette is then introduced into an EBV vector such as the pBD149 vector (10).

In either case, the siRNA cassettes are verified by sequencing.

The presence of the siRNA cassettes (H1 promoter+sequence encoding an shRNA) is verified by sequencing, recovered after digestion with the Kpn I/BamH I enzymes (New England Biolabs) and introduced into a pBD149 vector (10). Direct cloning into the pEBV vectors carrying the H1 promoter without shRNA sequence is also effective according to the same strategy, i.e. a Bgl II/Hind III digestion of the pBD631 vector (pBD665, which carries the siRNA cassette in the sense opposite to that of the pBD631 vector or of the pBD884 vector; see table I) followed by the insertion of the paired oligodeoxynucleotides. The EBV vectors pBD631 and pBD665 carry the H1 promoter and the Bgl II/Hind III cloning sites in the two possible orientations. Thus, the clonings can be carried out directly in these pBD631 and pBD665 vectors without involving the pSUPER vector.

Construction of Integrative Vectors

Integrative plasmids according to the prior art are also constructed after deletion of the EBV sequences from the preceding plasmid (Hpa I/BstE II digestion, Klenow filling and self-ligation). The Klenow filling, which makes it possible to obtain blunt ends, is carried out according to the following protocol: after digestion of the pEBV-siRNA vectors with the Hpa I then BstE II restriction enzymes (New England Biolabs, according to the supplier's recommendations), 1 mM of each dNTP (50 µm final concentration for each) and 1 unit of Klenow enzyme (Klenow 3'→5' exofragment; 5 U/µL) are added. The samples are incubated at ambient temperature for 15 min and the reaction is stopped by heating at 75° C. for 10 min.

The vectors used are listed in table I below.

TABLE I

| Genes targeted | pEBV reverse vectors | Resistance | SiRNA* | pEBV direct vectors | pHygro vectors | pSUPER vectors |
|---|---|---|---|---|---|---|
| Empty vector | pBD631 (pEBVsiR) | Hygromycin B | | pBD665 (pEBVsiD) | pBD641 (pHygrosi) | pBD621 (pSUPERsi) |
| | pBD884 (pEBVsiR-Puro) | Puromycin | | | | |
| Cloning vector | pBD751 (pEBVsiR-LacZ') | Hygromycin B | LacZ'for cloning | | | |
| | pBD899 (pEBVsiR-LacZ'-Puro) | Puromycin | | | | |
| Control vector | pBD650 (pEBVsiControlR) | Hygromycin B | Control (mutated shRNA) | | pBD653 (pHygrosiControl) | pBD647 (pSUPERsiControl) |
| | pBD886 (pEBVsiControlR-Puro) | Puromycin | | | | |
| KIN17 | pBD674 (pEBVsiK180R) | Hygromycin B | siK180 180-198 | pBD678 (pEBVsiK180D) | | pBD667 (pSUPERsiK180) |
| | pBD901 (pEBVsiK180R-Puro) | Puromycin | | | | |
| KIN17 | pBD685 (pEBVsiK406R) | Hygromycin B | siK406 406-424 | pBD686 (pEBVsiK406D) | | pBD645 (pSUPERsiK406) |
| | | Puromycin | | | | |
| KIN17 | pBD632 (pEBVsiK663R) | Hygromycin B | siK663 663-681 | pBD664 (pEBVsiK663D) | pBD642 (pHygrosiK663) | pBD622 (pSUPERsiK663) |
| | pBD900 (pEBVsiK663R-Puro) | Puromycin | | | | |
| KIN17 | pBD676 (pEBVsiK906R) | Hygromycin B | siK906 906-924 | pBD680 (pEBVsiK906D) | | pBD668 (pSUPERsiK906) |
| XPC | pBD634 (pEBVsiXPC-267R) | Hygromycin B | siXPC-267 267-285 | | pBD657 (pHygrosiXPC267) | pBD624 (pSUPERsiXPC267) |
| | pBD894 (pEBVsiXPC-267R-Puro) | Puromycin | | | | |
| XPA | pBD695 (pEBVsiXPA-587R) | Hygromycin B | siXPA-587 587-505 | | | pBD668 (pSUPERsiXPA587) |
| | pBD895 (pEBVsiXPA-587R-Puro) | Puromycin | | | | |
| XRCC4 | pBD694 (pEBVsiXRCC4-674R) | Hygromycin B | siXRCC4-674 674-692 | | | |
| | pBD902 (PEBVsiXRCC4-674R-Puro) | Puromycin | | | | |
| Ku70 | pBD699 (pEBVsiKu70-156R) | Hygromycin B | siKu70-156 156-174 | | | |
| | pBD903 (pEBV-siKu70-156R-Puro) | Puromycin | | | | |
| DNA-PKcs | pBD743 (pEBVsiDNAPK-5980R) | Hygromycin B | siDNAPK-5980 5980-5998 | | | |
| | pBD904 (pEBV-siDNAPK-5960R-Puro) | Purmocyin | | | | |
| Rad50 | pBD872 (pEBVsiRad50-274R) | Hygromycin B | Rad50-274 274-292 | | | |
| | pBD906 (pEBVsiRad50-274R-Puro) | Puromycin | | | | |
| Rad51 | pBD864 (pEBVsiRad51-114R) | Hygromycin B | siRad51-114 114-132 | | | |
| | pBD917 (pEBVsiRad51-114R-Puro) | Puromycin | | | | |
| Rad52 | pBD876 (pEBVsiRad52-502R) | Hygromycin B | Rad 52-502 502-520 | | | |
| | pBD910 (pEBVsiRad52-502R-Puro) | Puromycin | | | | |
| hHR23B | pBD804 (pEBVsiR23B-1123R) | Hygromycin B | siR23B-1123 1123-1141 | | | |
| | pBD896 (pEBVsiR238-1123R-Puro) | Puromycin | | | | |
| hHR23A | pBD805 (pEBVsiR23A-491R) | Hygromycin B | siR23A-491 491-509 | | | |
| | pBD897 (pEBVsiR23A-491R-Puro) | Puromycin | | | | |
| p53 | pBD848 (pEBVsip53-112R) | Hygromycin B | sip53-112 112-130 | | | |
| | pBD906 (pEBVsip53-112R-Puro) | Puromycin | | | | |
| hTER7 | pBD839 (pBSVsihTERT-1730R) | Hygromycin B | sihTERT-1730 1730-1748 | | | |
| | pBD905 (pEBVsihTERT-1730R-Puro) | Puromycin | | | | |
| SAF-A | pBD775 (pEBVsiSAFA-1955R) | Hygromycin B | siSAFA-1955 1955-1973 | | | |
| | pBD907 (pEBVsiSAFA-1955R-Puro) | Puromycin | | | | |

*the sequences are specified in table II.

Control plasmids are also constructed:
plasmids which carry an H1 promoter without siRNA (pBD631 and pBD665 mentioned above),
plasmids which carry an H1 promoter and a LacZ' cloning system without siRNA (pBD751 and pBD899 mentioned above),
a plasmid obtained after insertion of an shRNA carrying two mismatches on one of the strands of the hairpin structure (pBD650).

The plasmid DNA is purified with an anion exchange resin (Qiagen) and transfected.

The various siRNAs for XPA, XPC, $_{HSA}$kin17, XRCC4, Ku70, DNAPK, Rad50, Rad51, Rad52, hHR23B, hHR23A and p53 are constructed according to the recognized rules for siRNAs (2, 3, 16-18).

The synthetic DNA sequences encoding the shRNA sequences are adapted from the model described by Brummelkamp et al. (5) with CCG in the 5' position, as transcription initiation site, and 6 thymidines in the 3' position, as termination signal, and are introduced into the empty vector according to the invention as specified above, in the two possible orientations, in order to verify the role of their position relative to the other elements present in said vector.

In table I, the name of each siRNA sequence corresponds to:
si: siRNA
K: $_{HSA}$kin17
XPA: XPA
XPC: XPC
number: position of the 1st nucleotide in the siRNA sequence relative to the corresponding cDNA: for example, for KIN17: "siK108" signifies an siRNA sequence against the KIN17 mRNA which recognizes, as first nucleotide, the 180th of the sequence of the KIN17 cDNA (and the other 18 which follow).

The siRNAs were designed in accordance with the recommendations in the literature. In particular, the constructs take into account or do not take into account the thermodynamic characteristics of siRNA sequences (2, 3, 16, 17).

TABLE II specifies some of the siRNA sequences used.

| Sequence of the siRNA Position of the siRNA in the cDNA | Gene |
|---|---|
| TCCTCAGCAGTTTATGGAT (SEQ ID NO: 4) 180-198 | Kin17 |
| GGATGAAGCCCTCAGCGAT (SEQ ID NO: 5) 267-285 | XPC |
| GTCAAGAAGCATTAGAAGA (SEQ ID NO: 6) 587-605 | XPA |
| GAGATCCAGTCTATGATGA (SEQ ID NO: 7) 674-692 | XRCC4 |
| GAGTGAAGATGAGTTGACA (SEQ ID NO: 8) 156-174 | Ku70 |
| GTTGAGGTTCCTATGGAAA (SEQ ID NO: 9) 5980-5998 | DNA-PK |
| GAACTTATAGCTGTGCAAA (SEQ ID NO: 10) 274-292 | Rad50 |
| GAAGAAATTGGAAGAAGCT (SEQ ID NO: 11) 114-132 | Rad51 |
| GACAAAGACTACCTGAGAT (SEQ ID NO: 12) 502-520 | Rad52 |
| GCATTAGGATTTCCTGAAG (SEQ ID NO: 13) 1123-1141 | HR23B |
| AGACGATGCTGACGGAGAT (SEQ ID NO: 14) 491-509 | HR23A |
| CAAGCAATGGATGATTTGA (SEQ ID NO: 15) 112-130 | p53 |

Example 2

Compared Effectiveness of the siRNA Duplexes, of the Integrative Plasmids and of the Vectors Comprising an EBV Segment Inhibition of KIN17 Gene Expression In order to be able to compare the effectiveness of the inhibition of the expression of a gene, with various types of constructs, siRNA duplexes (siK180 and siK906) and the DNA sequences encoding the associated shRNAs were synthesized, respectively, by Ambion for the siRNAs and Eurogentec or Proligo for the DNAs. The DNA sequences encoding the shRNAs were introduced as described above into EBV vectors, giving the vectors pBD674 (or pBD678) and pBD676 (or pBD680) according to the orientation of the siRNA cassette. This approach makes it possible to compare the effectiveness of the pEBV-siRNA vectors compared with the siRNA duplexes from which they derive, after transfection into HeLa or RKO cells, under the conditions specified in the legend of FIG. 2.

Three days after the transfection, a decrease in the amount of $_{HSA}$kin17 protein of about 80-90% is observed, without modification of the other nuclear proteins tested (FIG. 2), thereby demonstrating the effectiveness of the pEBV-siRNA vectors according to the invention, which produce an extinction of the expression of the KIN17 gene similar to that observed after transfection of the siRNA duplexes. This also attests to the specificity of the repression since the level of the other control proteins is not modified.

The maintenance over time and the stability of the pEBV vectors (in the presence of hygromycin B) considerably improve the inhibition of expression of the genes tested, such as here the KIN17 gene (FIG. 3). The same is true of the XPA or XPC genes (see below).

The orientation of the siRNA cassette in the vectors does not affect the degree of inhibition of the expression.

Deletion of the EBV segment in the vectors results in the production of integrative plasmids (pHygro) of the type such as those described in the literature (see 5).

The effectiveness of the pEBV-siRNA vectors, according to the invention, in comparison with the existing vectors of integrative type (pHygro-siRNA), can be demonstrated according to two criteria: (1) the number of clones selected 14 days after transfection under clonogenic culture conditions (few cells placed in culture in the presence of hygromycin B), and (2) the number of cells of these clones that have been made effectively silent for the expression of a given gene (for example: KIN17). The results obtained are given in FIG. 4 and in table III hereinafter.

| | Number of clones ± SD per $10^6$ cells plated | |
|---|---|---|
| Vector | HeLa cells | RKO cells |
| pBD 631 pEBV-siR | 44250 ± 2136 | 42980 ± 2608 |
| pBD 632 pEBV-siK663R | 417 ± 144 | 37475 ± 1919 |
| pBD 650 pEBV-siControlR | 50833 ± 5700 | 46667 ± 5122 |
| pBD 641 pHygro-siR | 194 ± 48 | 2205 ± 287 |
| pBD 642 pHygro-siK663R | 56 ± 48 | 2205 ± 278 |
| pBD 653 pHygro-siControlR | 28 ± 48 | 17 ± 29 |

48 h after transfection, 150 cells (transfected by the vectors according to the invention) or 500 cells (transfected with pHygro vectors)/cm² (i.e. 5000 cells transfected with a pEBV vector according to the invention and 15 000 cells transfected with a pHygro vector) are plated in the presence of hygromycin B. Fourteen days later, the clones are fixed, stained and counted. Each point corresponds to the mean of three culture dishes. In the presence of an integrative vector (pHygro) similar to those encountered in the literature, few growing clones are observed after 14 days, and more than 50% of these clones do not inhibit expression of the KIN17 gene (FIG. 4.2).

On the other hand, many clones are observed after transfection with vectors according to the invention, all the latter inhibiting expression of the KIN17 gene (FIG. 4.4).

XPA and XPC

All the results correspond to a compilation of more than 10 independent tests, attesting to the reproducibility of these experiments, most of the experiments having been carried out in HeLa cells, and secondarily MRC5-V2 and RKO cells.

Tests similar to those carried out with KIN17 were undertaken with the XPA and XPC genes in HeLa, MRC5-V2 and RKO cells. The main results obtained are given in FIGS. 5 to 10 and they demonstrate the notable effectiveness of the vectors according to the invention for long-lasting and specific extinction of the expression of a gene, even after more than 260 days of culture.

The effectiveness of the vectors according to the invention is demonstrated during the random analysis of clones (in this case, 12 clones randomly chosen and in which expression of the XPA gene has been extinguished), where up to 100% of extinguished clones can be obtained 48 days after transfection (culture in the presence of hygromycin B). Such a result is never obtained with integrative vectors (type pHygro). In these experiments, the $XPC^{KD}$ clones (maintained for 113 days in continuous culture) serve as a control. It is, moreover, observed that the level of the other proteins analyzed does not change, attesting to the specificity of the extinction.

Verification of the Specificity and of the Stability Over Time

FIG. 6 illustrates the results of two simultaneous experiments, one analyzed in the medium term (after 15 days of continuous culture) and the second in the long and very long term (25 and 97 days of culture). In the two cases, the very high effectiveness and specificity of the constructs according to the invention is observed, with a greater than 95% reduction in the level of the target proteins such as XPA, kin17, XRCC4 or XPC (crossover trials).

These results show that the construct according to the invention functions irrespective of the shRNA sequence selected.

Particularly advantageously, 15 days after transfection (left side of FIG. 6), it is a question of analyzing cell populations (and not selected clones such as that which is shown on the right side of this same figure). This demonstrates the effectiveness of the vectors according to the invention for reducing, overall and in all the cells of a population (by definition heterogeneous), the level of expression of the target gene.

The clones selected and maintained in culture are regularly analyzed with respect to their principal phenotype associated with the loss of expression of the XPA and XPC proteins, i.e. their hypersensitivity to UVC. FIG. 7 demonstrates this with several $XPA^{KD}$ or $XPC^{KD}$ clones. Conversely, little or no specific sensitivity is observed after ionizing irradiation ($\gamma$-rays).

In addition, in order to verify that no nonspecific effect exists, empty vectors carrying the H1 promoter in the two different orientations without siRNA sequence (pBD631 and pBD665) and a pEBV vector (pBD650) containing an oligodeoxynucleotide encoding an shRNA carrying two mismatches in one of the strands of the hairpin structure were also tested.

These various vectors do not modify the expression of the gene (FIGS. 2-5).

Stability of the $XPA^{KD}$ and $XPC^{KD}$ Cells

As stated above, the stability of the clones maintained in culture is analyzed regularly in relation to their sensitivity to UVC. FIG. 8 demonstrates the hyper-sensitivity over time of the clones, even after 250 days of culture ($XPC^{KD}$ clone). It should be noted that, in the literature, no clone has achieved such a stability over time.

Conclusions

The vectors according to the invention induce extinction of the genes studied in more than 95% of the cells two weeks after transfection, whereas integrative vectors (pHygro-siRNA) induce less than 50% of extinguished cells after two weeks.

Most of the clones isolated do not express the target gene (100% for XPA).

More than 170 days after transfection, the selected clones continue to express the target gene very weakly.

The new phenotype associated with the loss of the target protein is thus maintained.

All the results are reproducible in various cell lines (HeLa, RKO, MRC5-V2) with various vectors according to the invention and irrespective of the shRNA (siRNA) selected.

Example 3

Long-Term Inhibition of XPA and XPC Gene Expression in Human Cells

The pEBV vectors according to the invention make it possible to obtain long-term expression inhibitions (see FIGS. 5 and 6, for example).

This can be explained by the characteristics of the selected plasmids, which persist in the nuclei as stable episomes after a long period of culturing.

The replication of the DNA of these vectors is semi-conservative, is initiated around the dyad (DS) and is coordinated with the genomic replication.

Cellular factors of the host aid the EBV replication. In particular, Orc2 interacts closely with the EBNA-1 sequence and restricts the EBV replication to a single round per cell cycle, thereby explaining why there are few copies of the vector/cell and considerable stability.

The presence of EBNA-1 also binds the EBV episomes at metaphase, which is a factor of their nuclear retention and their segregation during mitosis.

In addition, the EBV vectors according to the invention can behave like endogenous transcription units tightly controlling the siRNA transcription.

With these vectors, it is possible to isolate clones exhibiting undetectable levels of expression of the XPA and XPC genes (FIGS. 5 and 6).

It has already been possible to maintain these various $XPA^{KD}$ and $XPC^{KD}$ clones in culture for more than 260 days for the $XPC^{KD}$ clones and 170 days for the $XPA^{KD}$ clones.

In MRC5-V2 cells, $XPA^{KD}$, $XPC^{KD}$ and $KIN17^{KD}$ clones have also been in culture for more than 60 days.

The increased UV-sensitivity of the $XPA^{KD}$ and $XPC^{KD}$ cells illustrates the functional effectiveness of the vectors according to the invention.

It is thus possible to readily compare the phenotypes of the HeLA, HeLa $XPA^{KD}$ and HeLa $XPC^{KD}$ cells. In fact, these cells all have the same genetic information and differ only by virtue of the small shRNA sequence encoded by the vector according to the invention, and can be considered to be virtually isogenic (or quasi-isogenic) lines.

While the inhibition of the XPC gene, in HeLa cells, induces UVC-sensitivity (19 times more sensitive to 4 J/m$^2$ than the control cells), the cells which include the siRNA vectors against the XPA gene exhibit a smaller increase in UV-sensitivity (4 times).

The results are given in FIG. 7.

The $XPA^{KD}$ and $XPC^{KD}$ cells do not exhibit any significant sensitivity to ionizing radiation.

On the other hand, the $XPA^{KD}$ cells show a relatively rapid growth compared with the $XPC^{KD}$ cells in HeLa cells (FIG. 9) and in other cells (MRC5-V2).

This suggests that the partial loss of XPA does not significantly affect the cell physiology.

On the other hand, inhibition of the XPC gene leads to anomalies in the growth of the cells thus modified and only a few clones emerge from the cultures.

On the other hand, once established, the latter clones become notably stable.

Study of the Effect of Inhibition

The XPC$^{KD}$ cells exhibit spontaneous and UVC-induced micronuclei and also numerous apoptotic cells (as shown by the arrows in FIG. 10) after UVC irradiation, indicating an increase in genomic instability.

These results are given in table IV below and also in FIG. 10.

TABLE IV

|  | 0 J/m² | 20 J/m² |
|---|---|---|
| Control | 3% | 14% |
| BD695/3 (XPA$^{KD}$) | 3% | 39% |
| BD634/21 (XPC$^{KD}$) | 10% | 69% |
| BD634/24 (XPC$^{KD}$) | 13% | 59% |

XPA$^{KD}$: 148 days in culture
XPC$^{KD}$: 77 days in culture

Example 4

Study of the Effect of Selection Pressure: Advantage of the Model According to the Invention The cells transfected with the plasmids according to the invention are subjected to selection pressure (see example 2, table III).

The pEBV-siRNA vectors according to the invention are maintained in episomal form (not integrated into the genomic DNA) for many months. Thus, removal of the hygromycin B from the culture medium should allow the cells to lose this vector and to recover the expression of the gene previously extinguished (for example, XPC or XPA). It should be noted that this is strictly impossible in the case of conventional vectors of integrative type, where a large number of copies of these vectors are inserted into the genomic DNA.

In the case of the vectors according to the invention, and as demonstrated by the various experiments carried out, as soon as the hygromycin B is removed, the reversion occurs very rapidly (on average 7 to 10 days), as attested to by the immunocytochemical labelings, where 95-100% of the cells re-express the XPC or XPA proteins after only 7 days of culture in the absence of hygromycin B. This demonstrates a loss of the EBV-siRNA vectors simultaneously in all the cells in culture. This result is verified by analysis of the total DNA (genomic+episomal) by Southern blotting (FIG. 13). FIG. 13 demonstrates the following points:

(1) in the XPC$^{KD}$ and XPA$^{KD}$ clones, the pEBV-siRNA vectors are clearly maintained in an episomal form, (2) with a low copy number per cell (approximately 10), (3) the absence of hygromycin B for 10 days brings about the rapid and total loss of these vectors, thereby explaining the very rapid recovery of the expression of the XPC or XPA genes observed by immuno-cytochemistry.

This total and rapid reversion makes it possible to demonstrate that the loss of expression of a given gene can induce unexpected collateral effects.

For the first time, this is a means of testing the parallel consequences, unforeseeable at the start, of the effects of an siRNA sequence. It is not a question of demonstrating non-specific targets (off targets) already determined elsewhere, but to determine the real, specific and collateral effects of the loss of expression of a given gene. In practice, this is demonstrated by using the vectors according to the invention, and more particularly for the extinction of the XPC gene, where the reversion does not make it possible to recover the entire starting phenotype.

This property can in particular be used for restoring the starting phenotype in the case of a fine study to screen for siRNAs and specifying more clearly the possible side effects of the inhibition of expression of the targeted gene, in the long term.

Example 5

Analysis of the Activity of Active Multi-Protein Complexes In Vitro in Isogenic Clones (or Populations) which Derive Only by Virtue of the (Almost Total) Loss of Expression of an Essential Gene: Use of a Cell Model in Accordance with the Invention (Cells Modified with a Suitable Vector According to the Invention)

The obtaining of very stable clones after several months of culture, and even after freezing/thawing steps, makes it possible to obtain sufficient biological material to carry out experiments requiring many cells (>1-2×10$^7$ cells per point). In particular, and for the first time, it is possible to amplify the cells of a clone rendered silent for a gene (KIN17 in this example) through the use of a vector according to the invention, and to analyze, in vitro, its DNA repair activities.

In FIG. 16, preliminary tests show the feasibility of this approach were carried out. It should be noted that this approach is not possible after a transient transfection of siRNA duplex or of integrative vectors, in the sense that it would be necessary to transfect an enormous number of cells (very expensive) and it would be very difficult to obtain stable clones.

The use of vectors according to the invention therefore makes it possible, for the first time, to analyze the activity of active multiprotein complexes, in vitro, in isogenic clones (or populations) which derive only by virtue of the (almost total) loss of expression of an essential gene. In fact, with the vectors according to the invention, this can be undertaken rapidly, for example 15 days after transfection, i.e. at the moment when a very high degree of homogeneity of the cell populations under selection is already observed. These kinetics depend, of course, on the gene that it is desired to "extinguish", for example, this can be carried out very rapidly after transfection and hygromycin B selection in the case of XPA (example of silencing described above). This approach can of course be undertaken after the establishment of clones because they are stable (for example, XPA, XPC or KIN17).

Example 6

Vectors According to the Invention

1. Construction of the Cloning Vectors

Vector pBD751: The "promoter T7-LacZ"' fragment of the p205GTI vector (Stary et al., J Virol. 1989 September; 63(9): 3837-43.) was amplified by PCR with the following primers: 5' GGT ACC AGA TCT GAT CCG AAA TTA 3' (SEQ ID NO: 16) (containing a Bgl II site) and 5' GTC GAC AAG CTT TTG ATC AGA TCG GTG CGG (SEQ ID NO: 17) (containing a Hind III site), and then digested with Bgl II/Hind III and introduced into the pBD631 vector, itself digested with Bgl II/Hind III.

Vector pBD889: The "PuroR+SV40 promoter" fragment comes from the vector of De la Luna et al. (Gene 62, 121-126, 1988, Efficient transformation of mammalian cells with constructs containing a puromycin-resistance marker) in which the Hind III site located between the SV40 promoter and the puromycin-resistance gene (PuroR) has been deleted by Hind III digestion and treatment with the Klenow fragment, followed by religation. The vector obtained was called pBD881. The pBD881 vector was digested with the BamH I/EcoR I restriction enzymes in order to remove the PuroR fragment, which was introduced into an EBV vector, called pBD152 and derived from the vector pBD149 already mentioned; this vector contains the entire EBV sequence (EBNA-1+origin of replication). This new vector (pBD883 or pEBV-Puro) was digested with the EcoR V/BamH I restriction enzymes in order to recover the fragment containing the EBV part, the bacterial part and the SV40-PuroR promoter sequence; this fragment was ligated with the EcoR V/BamH I fragment of the pBD650 vector, so as to create the control vector pBD886 or pEBVsiControlR-Puro. Finally, the pBD886 vector was digested with the Hind III/BamH I restriction enzymes in order to introduce the H1 promoter-T7-LacZ' cloning fragment of the pBD751 vector; this new vector was called pBD899 or pEBVsiR-LacZ'-Puro.

2. Construction of the pBD884 Empty Vector (pEBVsiR-Puro)

The pBD884 vector was obtained by Spe I/BamH I digestion of the pBD883 vector (purification of the EBV-Puro part) and ligation with the Spe I/BamH I fragment of the pBD631 vector (H1-Bgl II/Hind III cloning sites). The pBD884 vector is therefore the homologue of the pBD631 vector, the first carrying the hygromycin B resistance and the second carrying the puromycin resistance.

3. Results

FIG. 17 shows the advantage of these cloning vectors. The insertion of the oligonucleotides (64-mer) into the pBD751 (or pBD899) vector is obtained with an efficiency close to 100%, thereby considerably reducing the number of bacterial clones to be analyzed. Usually, 3 to 6 bacterial clones ("white" colonies) are taken randomly and the plasmid DNAs thereof are isolated and analyzed. In most cases, these clones carry the recombinant plasmid (FIG. 17C). The cloning efficiencies are extremely reproducible.

Example 7

Extinction of the DNA-PKcs and XRCC4 Genes

No human mutant for the XRCC4 protein exists naturally. For the first time, the obtaining of "mutant" clones in which the level of expression of the XRCC4 protein is extremely low (approximately 10% of the normal level) is described; in parallel, a clone in which the DNA PKcs protein, a partner of XRCC4 in the NHEJ and V(D)J recombination pathways, is no longer detectable with the techniques used (immunocytochemical labeling, Western blotting) is also described. These clones have been maintained in culture for more than 130 days. In parallel to the very large reduction in the level of these two proteins in HeLa cells in the presence of the pBD694 and pBD743 vectors, the loss of the specific activities of these proteins is demonstrated: FIG. 19 demonstrates the total loss of DNA PKcs activity in the DNA PKcs$^{KD}$ clone and FIG. 20 demonstrates the loss of the DNA repair activity of the XRCC4$^{KD}$ and DNA PKcs$^{KD}$ clones in a specific in vitro test for NHEJ recombination.

FIGS. 18 to 20 therefore show the advantage of these vectors in the very-long-term extinction of the DNA-PKcs and XRCC4 proteins, associated with the loss of the corresponding biological activity.

Example 8

Extinction of the p53, hRad50, hHR23A and hHR23B Genes

Other genes of interest were studied as targets of the pEBVsiRNA vectors according to the invention, such as the p53, hRad50, hHR23A and hHR23B genes. FIG. 21 demonstrates that pEBVsiRNA vectors specific for these genes according to the invention are also very effective in HeLa cells. There does not therefore appear to be any limitation on the nature of the targeted genes.

Example 9

Short-, Medium- and Long-Term Extinction of Gene Expression

FIG. 22 summarizes various experiments carried out in concert, and demonstrates the effectiveness of the pEBVsiRNA vectors according to the invention in extinguishing the expression of specific genes (in this case, XPA, KIN17, XPC, XRCC4) at various times after transfection (and hygromycin B selection) of HeLa cells. These vectors are therefore extremely effective in the short, medium and very long term.

REFERENCES

1. McManus M. T. et al., *Nat Rev Genet*, 2002, 3, 737-47.
2. Schwarz D. S. et al., *Cell*, 2003, 115, 199-208.
3. Elbashir S. M. et al., *Nature*, 2001, 411, 494-8.
4. Hasuwa H. et al., *FEBS Lett*, 2002, 532, 227-30.
5. Brummelkamp T. R. et al., *Science*, 2002, 296, 550-3.
6. Anonymous, *Nat. Cell Biol.*, 2003, 5, 489-490.
7. Butz K. et al., *Oncogene*, 2003, 22, 5938-45.
8. Laposa R. R. et al., *Cancer Res*, 2003, 63, 3909-12.
9. Paddison P. J. et al., *Genes Dev*, 2002, 16, 948-58.
10. Biard D. S. et al., *Exp Cell Res*, 1992, 200, 263-71.
11. Calos M. P., *Trends Genet*, 1996, 12, 463-6.
12. Okuda Y. et al., *DNA Repair (Amst)*, 2004, 3, 1285-95.
13. Wakasugi M. et al., *J. Biol. Chem.*, 1999, 274, 18759-68.
14. Masson C. et al., *Proc. Natl. Acad. Sci. USA*, 2003, 616-621.
15. Angulo J. F. et al., *DNA Conformation and Transcription* (E. Takashi, Ed.), Landes Biosciences, Ohyama, Konan University, 2004.
16. Khvorova A. et al., *Cell*, 2003, 115, 209-16.
17. Tuschl T., *Chembiochem*, 2001, 2, 239-45.
18. Chalk A. M. et al., *Biochem Biophys Res Commun*, 2004, 319, 264-74.
19. Scacheri P. C. et al., *Proc Natl Acad Sci USA*, 2004, 101, 1892-7.
20. Collins C M. et al., *Adv Cancer Res*, 2002, 84, 155-74.
21. Dhar S. K. et al., *Cell*, 2001, 106, 287-296.
22. Chaudhuri B. et al., *Proc Natl Acad Sci USA*, 2001, 98, 10085-9.
23. Schepers A. et al., *Embo J*, 2001, 20, 4588-602.
24. Kapoor P. et al., *J Virol*, 2003, 77, 6946-56.
25. Friedberg E. C. et al., *DNA Repair and Mutagenis*, ASM Press, 1995.
26. Muotri A. R. et al., *Carcinogenisis*, 2002, 23, 1039-46.
27. Soutschek J. et al., *Nature*, 2004, 432, 173-178.

28. Bantounas I. et al., *J. Mol. Endocrinol*, 2004, 33, 545-557.
29. Dykxhoorn D. et al., *Nature Reviews*, 2003, 4, 457-467.
30. Barquinero J. et al., *Gene Therapy*, 2004, 11, 53-59.
31. Gilmore I. R. et al., *J. Drug Targeting*, 2004, 12, 6, 315-340.
32. Biard D. S. et al., *BBA*, 1992, 1130, 68-74.
33. *Biofutur*, 2002, 228, 52-61.
34. Voorhoeve et al., *TIBS*, 2003, 21, 2-4.
35. Sui G. et al., *Proc Natl Acad Sci USA*, 99, 5515-5520.
36. Dubois-Dauphin M. et al., *J. Comp. Neurol*, 2004, 474, 108-122.
37. Hu B. et al., *Virol. Methods*, 2004, 117, 129-136.
38. Liu B. H. et al., *Gene Ther.*, 2004, 11, 52-60.
39. Sato M. et al., *Mol. Ther.*, 2003, 8, 726-737.
40. Yates et al., *PNAS*, 1984, 81, 3806-3810.
41. Sugden et al., *Mol. Cell. Biol*, 1985, 5, 410-413.
42. Rawlins et al., *Cell*, 1985, 42, 859-868.
43. Reisman et al., *Mol. Cell. Biol*, 1986, 6, 3838-3846.
44. Lupton et al., *Mol. Cell. Biol*, 1985, 5, 2533-2542.
45. Reisman et al., *Mol Cell Biol*, 1985, 5, 1822-1832.
46. Wysokenski et al., *J. Virol*, 1989, 63, 2657-2666.
47. Chittenden et al., *J. Virol*, 1989, 63, 3016-3025.
48. Krysan et al., *Mol Cell. Biol*, 1991, 11, 1464-1472.
49. Krysan et al., *Mol Cell Biol*, 1989, 9, 1026-1033.
50. Gahn et al., *Cell*, 1989, 58-527-535.
51. Sexton et al., *J. Virol*, 1989, 63, 5505-5508.
52. Chalk A M et al., *NAR*, 2005, Database Issue, D131-4.
53. Yang Z G et al., *Biochemistry*, 2002, 41, 13012-13020.
54. Volker M. et al., *Mol. Cell*, 2001, 8, 213-224.
55. Sarasin et al., *Br. J. Dermatol*, 1992, 127, 485-491.
56. Daza et al., *Biol Chem.*, 1996, 377, 775-786.
57. Yates et al., *Nature*, 1985, 313, 812-815.
58. Biard D. et al., *J Biol Chem.*, 2002, 277, 19156-65.

What is claimed is:

1. An siRNA expression vector capable of inhibiting or extinguishing the expression of a target gene in a mammalian cell, which vector is characterized in that it comprises:
   (1) a bacterial cassette comprising a bacterial origin of replication and a bacterial selectable marker M1,
   (2) a cassette for selection in eukaryotic cells comprising a selectable marker M2 for eukaryotic cells, and in particular for mammalian cells, under the control of an appropriate promoter,
   (3) an EBV cassette comprising at least one fragment of the Epstein-Barr virus nuclear antigen 1 (EBNA-1), at least one fragment of the family of repeats (FR) and at least one fragment of the double symmetry (DYAD) region, and
   (4) an siRNA transcription cassette comprising at least one region encoding an siRNA corresponding to the target gene to be inhibited or to be extinguished, under the control of regulatory elements for transcription in mammalian cells, which regulatory elements include at least one promoter capable of transcribing an siRNA in mammalian cells and a transcription terminator; wherein said siRNA transcription cassette is immediately downstream of the transcription initiation site or else a maximum of at most 20 base pairs away from the latter; said transcription initiation site being CCG and said siRNA transcription cassette comprising, downstream of the sequence encoding the siRNA, a transcription terminator which comprises a sequence of 6 consecutive thymidines, in the sense strand of the construct.

2. The vector as claimed in claim 1, characterized in that the bacterial cassette (1) comprises a bacterial selectable marker M1 selected from the group consisting of markers for resistance to an antibiotic and auxotrophic markers.

3. The vector as claimed in claim 1, characterized in that the cassette for selection in eukaryotic cells (2) comprises a eukaryotic selectable marker M2 selected from the group consisting of markers for resistance to an antibiotic.

4. The vector as claimed in claim 3, characterized in that said selectable marker M2 is under the control of a suitable promoter, selected from the group consisting of the HSV thymidine kinase promoter and the SV40 promoter.

5. The vector as claimed in claim 1, characterized in that the promoter capable of transcribing an siRNA in mammalian cells is a promoter selected from the group consisting of the RNA polymerase III (type 1, 2 or 3) promoter or a promoter recognized by the RNA polymerase II.

6. The vector as claimed in claim 5, characterized in that said RNA polymerase III promoter is selected from the group consisting of the H1 RNA, U6 snRNA, 7SK RNA, 5S, adenovirus VA1, Vault, RNA telomerase and tRNA (Val, Met or Lys3) promoters.

7. The vector as claimed in claim 1, characterized in that said transcription cassette also comprises a selection system for the cloning of said vectors.

8. The vector as claimed in claim 7, characterized in that said system comprises a prokaryotic promoter, followed by the alpha fragment of the LacZ gene (LacZ' or LacZ alpha) constituting a criterion of selection during the insertion of an shRNA sequence.

9. A eukaryotic cell, characterized in that it is modified with a vector as claimed in claim 1.

10. A pharmaceutical composition, characterized in that it comprises a vector as claimed in claim 1, and at least one pharmaceutically acceptable carrier.

11. A kit, characterized in that it comprises at least one vector as claimed in claim 1, and means for detecting and/or quantifying the expression of a target gene.

* * * * *

SEQUENCE LISTING

```
<160> NUMBER OF SEQ ID NOS: 20

<210> SEQ ID NO 1
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ggaattcgaa cgctgacgtc atcaacccgc tccaaggaat cgcgggccca gtgtcactag      60
gcgggaacac ccagcgcgcg tgcgccctgg caggaagatg gctgtgaggg acagggagt     120 ggcgccctgc aatatttgca tgtcgctatg tgttctggga aatcaccata aacgtgaaat     180
gtctttggat ttgggaatct tataagttct gtatgagacc ac                        222

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccatggaatt cgaacgctga cgtc                                             24

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcaagcttag atctgtggtc tcatacagaa cttataagat tccc                       44

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4
tcctcagcag tttatggat                                              19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggatgaagcc ctcagcgat                                              19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtcaagaagc attagaaga                                              19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gagatccagt ctatgatga                                              19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gagtgaagat gagttgaca                                              19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gttgaggttc ctatggaaa                                              19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
```

-continued gaacttatag ctgtgcaaa                                              19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gaagaaattg gaagaagct                                              19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gacaaagact acctgagat                                              19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcattaggat ttcctgaag                                              19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agacgatgct gacggagat                                              19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
caagcaatgg atgatttga                                              19

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtaccagat ctgatccgaa atta                                        24

```
<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtcgacaagc ttttgatcag atcggtgcgg                                     30

<210> SEQ ID NO 18
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agatcccgtc aagtactctg ggaccgttca agagacggtc ccagagtact tgactttttt    60
ggaaa                                                                65

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aagcttttcc aaaaaagtca agtactctgg gaccgtctct tgaacggtcc cagagtactt    60
gacgg                                                                65

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Consensus
      binding sequence

<400> SEQUENCE: 20
agattaggat agctatgcta cccagatat                                      29
```